United States Patent [19]

Rosenberger et al.

[11] 3,972,896

[45] Aug. 3, 1976

[54] ARYL KETALS OF POLYCYCLIC OXO COMPOUNDS AND PROCESSES

[75] Inventors: Michael Rosenberger, Caldwell; Gabriel Saucy, Essex Fells, both of N.J.

[73] Assignee: Hoffmann-La Roche Inc., Nutley, N.J.

[22] Filed: June 9, 1975

[21] Appl. No.: 584,992

Related U.S. Application Data

[60] Division of Ser. No. 363,443, May 24, 1973, Pat. No. 3,907,827, which is a continuation-in-part of Ser. No. 74,519, Sept. 22, 1970, Pat. No. 3,758,509, which is a continuation-in-part of Ser. No. 11,023, Feb. 12, 1970, Pat. No. 3,708,500, which is a continuation-in-part of Ser. No. 825,389, May 16, 1969, abandoned, and Ser. No. 824,319, May 13, 1969, Pat. No. 3,544,600.

[52] U.S. Cl. ............................................. 260/340.5
[51] Int. Cl.² ...................................... C07D 317/44

[58] Field of Search .................................. 260/340.5

[56] References Cited
UNITED STATES PATENTS

| | | | |
|---|---|---|---|
| 3,655,695 | 4/1972 | Andrews | 260/340.5 |
| 3,816,536 | 6/1974 | Eder et al. | 260/340.5 X |

*Primary Examiner*—Ethel G. Love
*Attorney, Agent, or Firm*—Samuel L. Welt; George M. Gould; Raymond R. Wittekind

[57] ABSTRACT

The intermediates and processes of this disclosure provide a new stereo-specific total synthesis of steroidal materials having known valuable pharmacological properties. A fundamental feature of this disclosure is the utilization of aryl ketals, preferably phenylenedioxy ketals derived from catechol as protective groups for oxo moieties in the polycyclic intermediates used in the aforesaid total synthesis.

4 Claims, No Drawings

ARYL KETALS OF POLYCYCLIC OXO COMPOUNDS AND PROCESSES

RELATED APPLICATIONS

This application is a division of application Ser. No. 363,443, filed May 24, 1973, now U.S. Pat. 3,907,827, issued Sept. 23, 1975, which is a continuation-in-part of application Ser. No. 74,519, filed Sept. 22, 1970, now U.S. Pat. 3,758,509, issued Sept. 11, 1973, which is a continuation-in-part of application Ser. No. 11,023, filed Feb. 12, 1970 now U.S. Pat. 3,708,500, issued Jan. 2, 1973, which is a continuation-in-part of application Ser. No. 825,389, filed May 16, 1969, now abandoned, and application Ser. No. 824,319, filed May 13, 1969, now U.S. Pat. 3,544,600, issued Dec. 1, 1970.

DETAILED DESCRIPTION OF THE INVENTION

This invention is concerned with certain polycyclic compounds and with processes for their synthesis. More particularly this invention relates to novel derivatives of cyclopenta[f][1]benzopyrans and 7H-naphtho[2,1-b]pyrans, and to methods for their production. These compounds are useful as intermediates in syntheses of steroids and D-homosteroids, respectively. In syntheses of steroidal materials steric considerations are of great significance. The most used steroidal compounds are those havin a C/D-trans ring junction with the substituent in the 13-position being in the $\beta$-stereoconfiguration. The present invention provides a facile total synthesis of $13\beta$-C/D-transsteroidal materials. This desirable result is obtained via a unique asymmetric induction with optical specificity preserved in subsequent reaction steps. A particular aspect of this invention resides in the use of arylenedioxy ketals as protective groups for intermediate compounds in the synthesis of steroids. Arylenedioxy ketals exhibit unexpected advantages over other ketal protective groups, e.g., alkylenedioxy ketals in that the former groups are more stable to the reaction conditions employed in the synthesis thus providing substantially higher yields of desired end products. This is particularly true in the case of steps requiring oxidation in the presence of acid.

In a major aspect, this invention is concerned with novel derivatives of cyclopenta[f][1]benzopyrans having the tricyclic nucleus

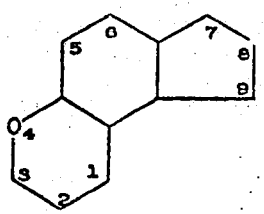

and novel derivatives of naphtho[2,1-b]pyrans having the tricyclic nucleus

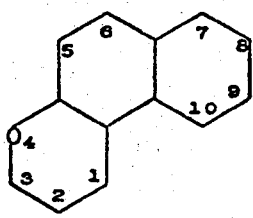

These novel compounds are generally defined by the formula:

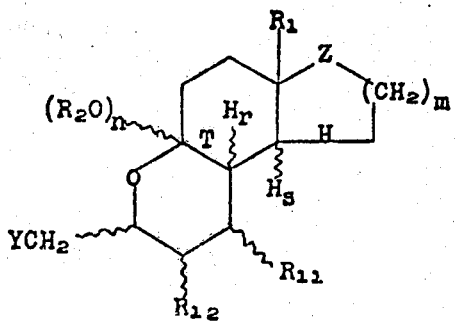

wherein Y is

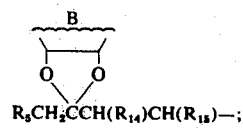

$R_sCH_2CCH(R_{14})CH(R_{15})-$;

B is the remaining residue of an aryl group which may be monocyclic or bicyclic and which may bear one or more additional substituents selected from the group consisting of lower alkyl and lower alkoxy; $R_1$ is a primary alkyl group of from 1 to 5 carbon atoms; $R_2$ is hydrogen, lower primary alkyl, or lower acyl; $R_5$, $R_{11}$, $R_{12}$, $R_{14}$ and $R_{15}$ are each independently hydrogen or lower alkyl; Z is carbonyl or a group of the formula

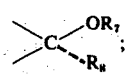

$R_7$ is hydrogen or lower acyl; $R_8$ is hydrogen or lower aliphatic hydrocarbyl; T represents either a single or a double bond; U represents a single or a double bond and is a single bond when T is a single bond; m is an integer having a value of 1 to 2; n is an integer having a value of from 0 to 1 and is 0 when T represents a double bond and is 1 when T represents a single bond; r is an integer having a value of from 0 to 1 and is 0 when T is a double bond and 1 when T is a single bond; and s is an integer having a value of from 0 to 1 and is 0 when U is a double bond and 1 when U is a single bond.

As used throughout the specification and appended claims, the term "hydrocarbyl group" denotes a monovalent substituent consisting solely of carbon and hydrogen; the term "hydrocarbylene" denotes a divalent substituent consisting solely of carbon and hydrogen and having its valence bonds from different carbons; the term "aliphatic", with reference to hydrocarbyl or hydrocarbylene groups, denotes groups containing no aromatic unsaturation, but which can be otherwise saturated or unsaturated, i.e., an alkyl or alkylene, or an aliphatic group containing olefinic or acetylenic unsaturation; the term "alkyl group" denotes a saturated hydrocarbyl group, whether straight or branched chain; the term "primary alkyl group" denotes an alkyl group having its valence bond from a carbon bonded to at least two hydrogens; the term "alkoxy" denotes the group R'O—, where R' is alkyl; the term "acyl group" denotes a group consisting of the residue of a hydrocarbyl monocarboxylic acid formed by removal of the hydroxyl portion of the carboxyl group; the term "oxyhydrocarbyl" denotes a monovalent saturated cyclic or acyclic group consisting of carbon, hydrogen, and oxygen containing only one oxygen in the form of an ether linkage; and the term "lower" as applied to any of the foregoing groups denotes a group having a carbon skeleton containing up to and including eight carbons, such as methyl, ethyl, butyl, tert.-butyl, hexyl, 2-ethylhexyl, vinyl butenyl, hexenyl, ethinyl, ethylene, methylene, formyl, acetyl, 2-phenylethyl, benzoyl, methoxymethyl, 1-methoxyethyl, tetrahydropyran-2-yl, methoxy, ethoxy, and the like.

In the formulas presented herein the various substituents on cyclic compounds are joined to the cyclic nucleus by one of three notations, a solid line (—) indicating a substituent which is in the β-orientation (i.e., above the plane of the paper), a dotted line (-------) indicating a substituent which is in the α-orientation (below the plane of the paper), or a wavy line (∼∼∼) indicating a substituent which may be in either the α- or β-orientation. The position of $R_1$ has been arbitrarily indicated as the β-orientation, although the products obtained in the examples are all racemic compounds unless otherwise specified.

Preferred compounds are those wherein Y is 3,3-(arylenedioxy)butyl wherein the arylenedioxy group, when taken with the 3-carbon of the butyl radical, forms a dioxolane ring system, especially 3,3-(phenylenedioxy)-butyl, 3,3-(2,3-naphthalenedioxy)-butyl and 3,3-(4,5-dimethylphenylenedioxy)-butyl; $R_1$ is n-alkyl, especially methyl and ethyl; and, when s has a value of 1, the 9α- (when m is 1) or 10α- (when m is 2) hydrogen is transoriented with respect to $R_1$.

Subgeneric to the tricyclic compounds of formula I are the 3-substituted 6aβ-alkyl-1,2,3,5,6,6a,7,8-octahydrocyclopenta[f][1]benzopyrans (by alternate nomenclature 3-substituted-6aβ-alkyl-2,3,5,6a,8-hexhydro-1H-cyclopenta[f][1]-benzopyrans) and the 3-substituted-6aβ-alkyl-1,2,5,6,6a,7,8,9-octahydro-3H-naphtho[2,1-b]pyrans (by alternate nomenclature 3-substituted-6aβ-alkyl-1,2,3,5,6,6a,8,9-octahydro-7H-naphtho[2,1-b]pyrans), hereinafter referred to as "dienes", having the formula:

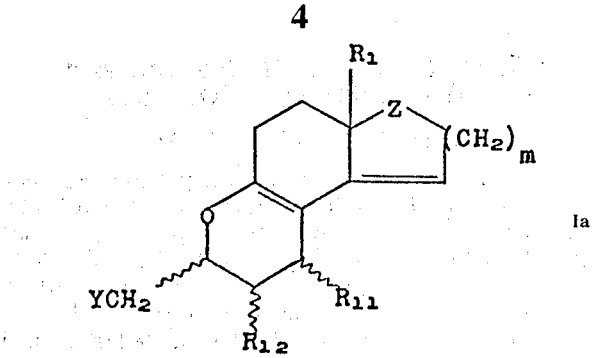

Ia wherein $R_1$, $R_{11}$, Z, Y and m are as defined above; the 3-substituted-6aβ-alkyl-1,2,3,5,6,6a,7,9,9,9a-decahydrocyclopenta[f][1]benzopyrans (by alternate nomenclature 3-substituted-6aβ-alkyl,2,3,5,6-,6a,8,9,9a-octahydro-1H-cyclopenta[f][1]benzopyrans) and the 3-substituted-6aβ-alkyl-1,2,5,6,6a,7,8,9,10,10a-decahydro-3H-naphtho[2,1-b]pyrans (by alternate nomenclature 3-substituted-6aβ-alkyl-1,2,3,5,6,6a,8,9,10,10a-decahydro-7H-naphtho[2,1-b]pyrans), hereinafter referred to as "monoenes" represented by the formula:

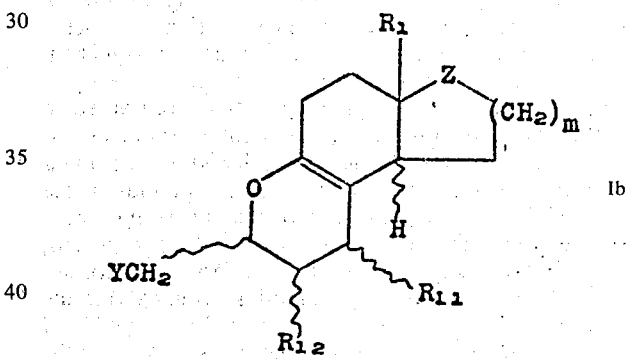

Ib wherein $R_1$, $R_{11}$, $R_{12}$, Z, Y, and m are as defined above; and the 3-substituted-6aβ-alkyl-4a-hydroxyperhydrocyclopenta[f][1]benzopyrans and the 3-substituted-6aβ-alkyl-4a-hydroxyperhydro-3H-naphtho[2,1-b]pyrans and their lower alkyl ethers an monoacyl esters, hereinafter referred to as "perhydro" compounds represented by the formula:

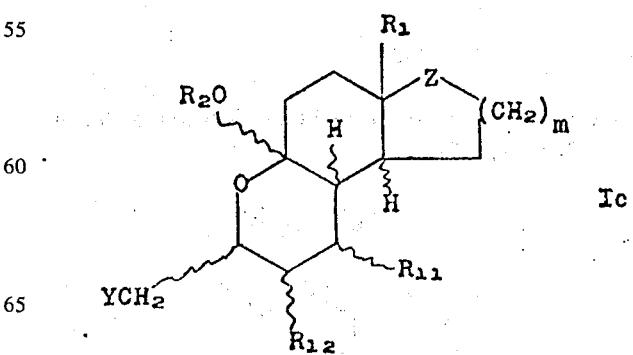

Ic wherein $R_1$, $R_2$, $R_{11}$, $R_{12}$, Z, Y and $m$ are as defined above.
This invention is concerned with a method for producing the compounds of formula I via the following general reaction scheme:
 + 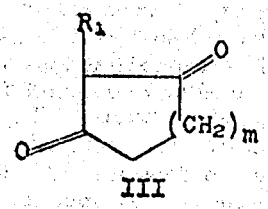
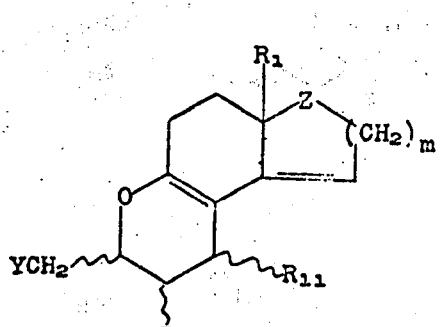 Ia
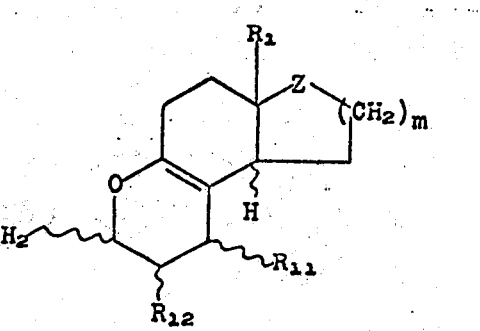 Ib
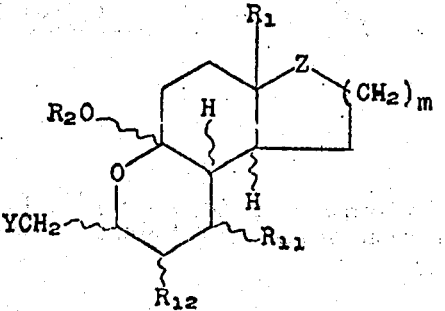 Ic wherein Y, $R_1$, $R_2$, $R_{11}$, $R_{12}$, Z, and m are as defined above; and V is hydrogen, lower alkyl or lower acyl.

Thus, the process of this invention comprises the general steps of (1) condensation of a substituted 7-hdyroxy-1-alken-3-one or a variant thereof (II), as defined below, with a 2-alkylcycloalkane-1,3-dione (III), as defined below, to produce diene (Ia); (2) saturation of the 9,9a- or 10,10a-double bond of diene (Ia) to produce monoene (Ib); and (3) introduction of a hydroxy, alkoxy, or acyloxy group at the 4a-position and a hydrogen atom at the 9b- or 10b-position of monene (Ib) to produce perhydro compound (Ic). It is to be understood that the foregoing reaction sequence is merely schematic in nature, and that each depicted step can represent only one or more than one reaction, as will be more fully described herein.

1-Alken-3-one compounds of formula II are employed as one of the starting materials for the foregoing reaction sequence. Illustrative examples of these 1-alken-3-ones include the 11,11-arylenedioxy-7-hydroxy-1-alken-3-ones, preferably 11,11-phenylenedioxy-7-hydroxy-1-dodecen-3-one.

The 11,11-arylenedioxy-7-hydroxy-1-dodecen-3-ones of formula II above or cyclic variations thereof are readily synthesized from 4,4-ethylenedioxy-1-chloropentane as per the following reaction sequence:

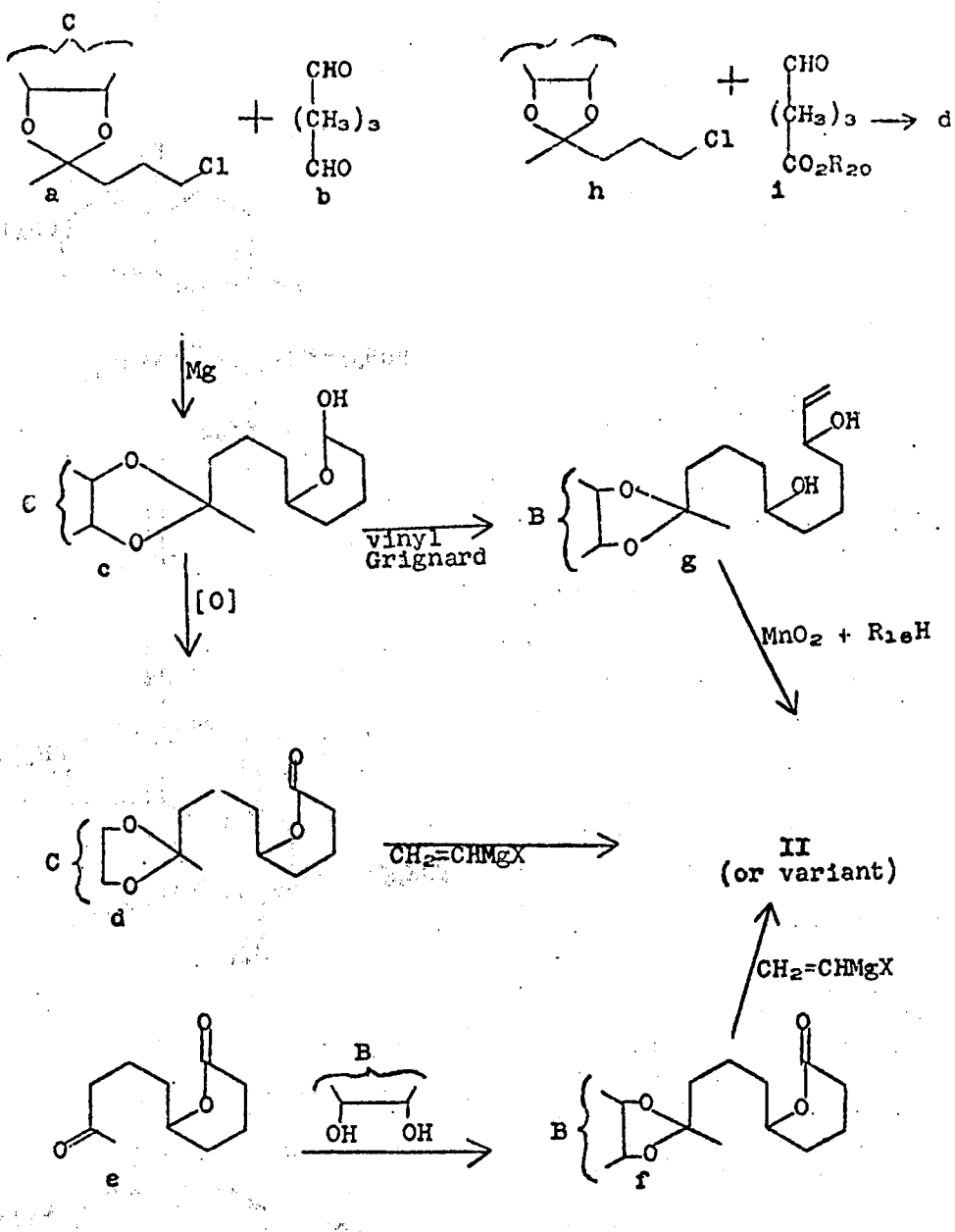

where B is as above, C is alkylenedioxy, preferably ethylenedioxy or arylenedioxy, preferably phenylenedioxy, X is a halide, preferably chloride, $R_{16}$ is as hereinafter described and $R_{20}$ is lower alkyl.

As indicated in the above sequence in one embodiment 4,4-alkylene- or phenylenedioxy-1- chloropentane (a) is converted to the Grignard by treatment with magnesium metal. This reaction may be activated by the addition of a crystal of iodine to the reaction medium. The Grignard is then reacted with glutaraldehyde (b) to yield a hemiacetal (c). Conversion of this hemiacetal to formula II compounds may be accomplished by alternative routes. In a first route, where C is B, the hemiacetal (c) is reacted with vinyl Grignard in an ethereal solvent, e.g., tetrahydrofuran at −20° to 10°C. to yield the vinyl hydroxy compound (g). Treatment of (g) with manganese dioxide and $R_{16}H$ at room temperature in a hydrocarbon solvent yields compounds of formula II.

The hemiacetal (c) may also be oxidized utilizing a chemical oxidizing agent, e.g., silver nitrate, bromine, sodium dichromate bihydrate or potassium dichromate to yield the lactone (d). It is preferable that when the ketal moiety C is arylenedioxy that the oxidizing agent used be other than bromine due to the possibility of bromination of the aromatic ring. It is also possible to oxidize the hemiacetal (c) catalytically using oxygen and a noble metal catalyst, e.g., platinum black. Where C is arylenedioxy in lactone (d), the lactone may be converted directly to compounds of formula II by reaction with vinyl Grignard in ethereal solvent, e.g., tetrahydrofuran at temperatures below 0°, preferably −70°C. to −45°C.

Where C in lactone (d) is alkylenedioxy, the lactone is treated with aqueous acid to hydrolyze the ketal group to form the keto lactone (e). Treatment of the keto lactone with the desired dihydroxy aryl compound such as, for example, catechol, 4,5-dimethylcatechol or a 1,2 or 2,3-naphthdiol, preferably in an inert organic solvent, e.g., an aromatic hydrocarbon such as benzene, toluene or xylene, preferably benzene under conventional conditions, e.g., at reflux.

The aforesaid ketalization reaction may produce a ketal half-ester as an intermediate which is readily convertible into the desired arylenedioxy lactone upon distillation.

Compounds of formula II are then obtained from said arylenedioxy lactones (f) by the selective addition of vinyl Grignard, e.g., vinyl magnesium chloride to the lactone at low temperatures, e.g., below 0°C., most preferably at about −45°C. in an inert organic solvent medium such as an etheric solvent, preferably diethyl ether, diisopropyl ether, tetrahydrofuran, dioxane or the like.

In an alternative procedure, ketal lactones of formula d wherein C is B may be conveniently prepared from the arylenedioxyketal (h) by reaction with a 5-oxo-pentanoic acid ester, e.g., the ethyl ester at a temperature of about −60°C. to −30°C. in tetrahydrofuran.

Because of the susceptibility of the vinyl grup of the 7-hydroxy-1-alken-3-one to decomposition, it is desirable, although not essential, that this compound be converted to more stable variants, such as those of the formula:

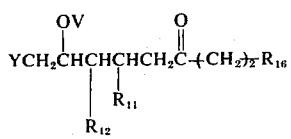

II-a wherein $R_{11}$, $R_{12}$, Y and V are as defined above; and $R_{16}$ is chloro, hydroxy, lower alkoxy, lower hydrocarbylamino or di(lower hydrocarbyl)amino.

As exemplary, these compounds of formula II-a are readily produced from the vinyl ketones of formula II by known techniques. For example, 1-chloro-7-hydroxyalkan-3-ones are obtained by the anti-Markownikoff reaction of the vinyl compound with hydrogen chloride in known manner. 1-Hydroxy and 1-alkoxy derivatives are obtained by the base-catalyzed reaction of water or a lower alkanol, for example, methanol, with the vinyl ketone. Additional derivatives are formed by the reaction of the vinyl ketone with a mono(lower hydrocarbyl)- or di(lower hydrocarbyl)-amine to form the Mannich base 1-(lower hydrocarbyl)amino- or 1-di(lower hydrocarbyl)amino-7-hydroxyalkan-3-one. A particularly advantageous procedure is to oxidize a hydroxy vinyl compound e.g. formula (g) with manganese dioxide in the presence of such an amine. In some instances, particularly in large scale commercial operation, it may be desirable to convert the Mannich base to its crystalline acid addition salts, particularly quaternary ammonium salts. All of the chloro, hydroxy, alkoxy, and aminoalkanones yield the alkenones of formula II under the conditions of the condensation with the 2-alkylcycloalkane-1,3-dione.

The compounds of formula II as is evident from the previously described reaction sequence can be used in the form of still another variant. This is the cyclized variant comprising a cyclic hemiketal, i.e., 2-tetrahydropyranol of the formula:

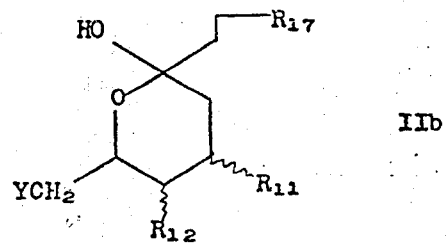

IIb wherein Y is as defined above and $R_{17}$ is lower hydrocarbylamino or di(lower hydrocarbyl)amino.

The variants of formula IIb can be prepared from compounds of formula II by reaction with the same reactants as are used to produce those compounds of formula IIa wherein $R_{16}$ is lower hydrocarbylamino or di(lower hydrocarbyl)amino. As is apparent, those compounds of formula IIa wherein $R_{16}$ has the aforesaid meanings and the compounds of formula IIb are isomers. These isomers exist in the form of a ketone of formula IIa or in the form of the cyclic hemiketal of formula IIb or as an equilibrium mixture of the two forms. Whether a particular Mannich base of formula IIa exists in that form or the hemiketal form or in an equilibrium mixture consisting primarily of one or the other will depend upon the environmental conditions in which it is placed, such as temperature, solvent, and pH of reaction medium, as well as the particular meaning of Y and $R_{16}$ or $R_{17}$. Either form is useful for the purposes of this invention since these isomers are used in a reaction with compounds of formula III, infra, and either the acyclic form of formula IIa or the cyclic hemiketal form of formula IIb is useful for this purpose. A particular advantage of the cyclic form is its greater stability as compared with the acyclic form and also as compared with the vinyl ketones of formula II. In order to obtain the cyclic form it is essential that in the compound of formula IIa, V is hydrogen. Acidic conditions shift the equilibrium away from the cyclic form. Use of an optically active amine, e.g., α-phenylethylamine, offers the advantage of resolving the compound, for example, via salt formation, e.g., the oxalate salt, to give an optically pure isomer of formula IIa or IIb which is then used either in the form of the free base, as the salt or as a lower alkanol adduct, e.g., methanol adduct in the remainder of the reaction sequence of this invention and when coupled with the unique asymmetric induction and preservation of optical specificity thereof offers a facile route to optically pure steroidal materials.

As is indicated above, the 7-hydroxy group of the 7-hydroxydodecanone of formula II or IIa can be esterified or etherified for the condensation reaction with the cycloalkanedione. These reactions can be effected in known manner. For example, the 7-hydroxyalkan-3-one can be reacted with a carboxylic acid or an acid chloride to produce an ester, or can be converted to an ether by either (1) preferably known acid catalyzed etherifications, e.g., with isobutylene or dihydropyran or (2) conversion of the 7-hydroxyalken-3-one to its sodium salt followed by reaction of the salt with an alkyl halide. In the event $R_8$ is hydrogen, this hydroxyl group is also etherified or esterified.

The starting material of formula II or variant thereof can either be used in racemic form or in optically active form. When used in optically active form, the 7S-antipode is preferred for reasons more fully explained below.

The second reactant employed in the condensation as generall mentioned above is 2-(lower alkyl)cycloalkane-1,3-dione of the formula:

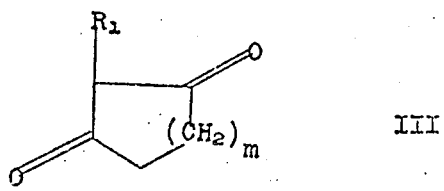

III wherein $R_1$ and $m$ are as defined above. These compounds are known compounds and description of their synthesis is accordingly unnecessary. Suitable compounds include 2-methylcyclopentane-1,3-dione, 2-ethylcyclopentane-1,3dione, 2-propylcyclopentane-1,3-dione, 2-butylcyclopentane-1,3-dione, 2-methylcyclohexane-1,3-dione, and the like.

The conditions for the condensation of ketone (II) or variant (IIa or IIb) with cyclic dione (III) are not narrowly critical, although it is preferred, particularly when the acyclic ketone is charged as the vinyl ketone, that a non-oxidizing atmosphere, e.g., nitrogen or argon, be employed. It is further preferred that an antioxidant, for example, phenolic compounds such as hydroquinone, be present. Furthermore, the reaction can be conducted in the absence or presence of acid or base promoters. Suitable basic promoters include those heretofore known to promote the Michael condensation, including inorganic bases, for example, alkali metal hydroxides, such as sodium hydroxide or potassium hydroxide, and organic bases, including alkali metal alkoxides, for example, sodium or potassium methoxide or ethoxide, and ammonium hydroxides, particularly benzyltrialkylammonium hydroxide. A preferred class of base promoters are the amines, especially tertiary amines and most preferably pyridine-type compounds such as pyridine and the picolines. Acid promoters which can be employed include organic carboxylic acids such as acetic acid or benzoic acid; organic sulfonic acids such as p-toluenesolfonic acid; and mineral acids such as sulfuric acid, phosphoric acid, hydrochloric acid, and the like. The amount of promoter employed is not narrowly critical and can vary from catalytic amounts to molar amounts.

The ratio of ketone (II) or variant (IIa or IIb) to cyclic dione (III) is not narrowly critical, although approximately equimolar amounts are preferred. Although there is no particular advantage to the use of excesses of either reactant, the cycloalkanedione can be more readily employed in excess because, due to its general low solubility in known organic solvents, unreacted cycloalkanedione can be easily recovered from the reaction mixture.

The reaction temperature is not critical and can vary from room temperature or below to reflux temperature or higher. The condensation is preferably conducted in the presence of an inert solvent to insure a fluid reaction mixture and uniform reaction temperatures. Suitable solvents include tertiary alcohols such as tert.-butanol; aliphatic and aromatic hydrocarbons such as cyclohexane, hexane, octane, benzene, xylene, toluene, and the like; ethers such as diethyl ether, tetrahydrofuran, and the like; chlorinated hydrocarbons such as carbon tetrachloride, chloroform, and the like; as well as dipolar aprotic solvents such as dimethyl sulfoxide and the N,N-disubstituted amides such as dimethylformamide or dimethylacetamide.

The product of the condensation, depending upon the nature of vinyl ketone or variant (II, IIa or IIb) and/or the reaction promoter employed, can be one or more of the compounds having the formulae:

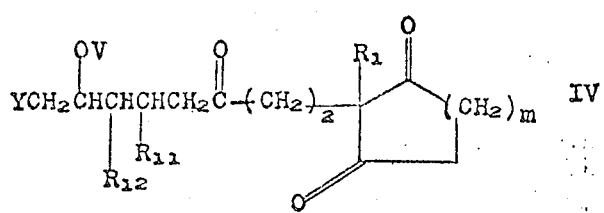   IV

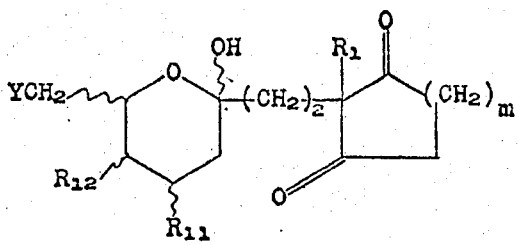

V

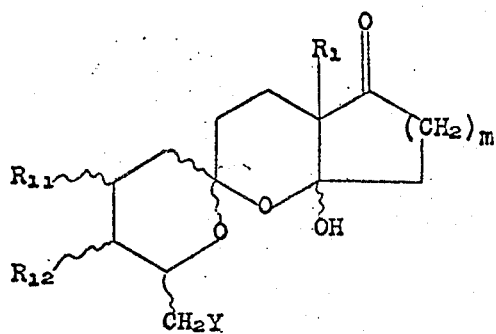

VI

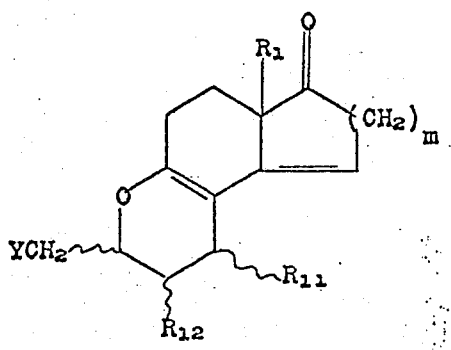

Ia-1 wherein $R_1$, $R_{11}$, $R_{12}$, V, Y, and $m$ are as defined above.

When vinyl ketone (II) is a 7-alkoxy- or 7-acyloxy compound, the product will be a compound of formula IV. However, when the vinyl ketone is a 7-hydroxy compound, or the reaction conditions are sufficient to convert a 7-alkoxy- or 7-acyloxy group, if present, the product will depend upon the promoter.

When the promoter is an acid or a relatively weak base, such as pyridine, or when no promoter is employed at all, the reaction product obtained from the 7-hydroxy vinyl ketone is the diene, i.e., tricyclic enol ether (Ia-1). When a strong base, such as sodium or potassium hydroxide, is employed as a promoter, a crystalline product having the formula VI is isolated, although compounds of formulae IV and V are also present in the reaction mixture. However, the compounds of formulae IV, V and VI, upon treatment with an acid, such as acetic acid, para-toluenesulfonic acid, or sulfuric acid, readily form the diene, i.e., tricyclic enol ether (Ia-1). It should also be noted that the conversion of the acyloxy or alkoxy groups of compound (IV) to a hydroxy group in an acidic medium is accompanied by cyclization to enol ether (Ia-1).

The condensation of a vinyl ketone of formula II or a variant thereof of formula IIa or IIb with a cycloalkanedione of formula III is one of the key features of this reaction. It is in this condensation that specific stereochemical induction at one member of the critical C/D-ring junction of the eventual steroidal product occurs. Thus, this invention is particularly advantageous in that it involves a unique asymmetric induction. Thus, the products of the condensation, i.e., the dienones of Ia-1, Ia-l, have at least two asymmetric centers at positions 3 and 6a permitting theoretically of two racemates or four optical antipodes. However, as a result of the condensation of this invention, when using a racemic starting material of formulas II, IIa or IIb wherein $R_{11}$ and $R_{12}$ are both hydrogen only a single racemate of formula Ia-1 results and when using an optically active starting material or formulas II, IIa or IIb wherein $R_{11}$ and $R_{12}$ are both hydrogen only a single optical antipode of formula Ia-1 results. It has further been found that when starting with a compound of formula II or IIa with a 7S-stereoconfiguration or of formula IIb with corresponding stereoconfiguration there is obtained the more desirable optical antipode of formula Ia-1 having a 6a$\beta$-stereoconfiguration. Thus, to prepare steroidal materials having the more desired 13β-stereoconfiguration by the synthesis of this invention one can either start with the antipode of formula II, IIa or IIb, which can be prepared by resolving a racemic compound of formula II, IIa or IIb, or one can resolve at some intermediate stage subsequent to the condensation with a cycloalkanedione of formula III or one can resolve the end-product steroidal material. In any event, the unique asymmetric induction concurrent to the condensation of this invention renders the obtention of a single optical antipode as an end-product more facile. The simultaneous formation of the dienol ether of formula Ia-1 with unique asymmetric induction is a special advantage of this invention.

The dienes of formula Ia in the presence of water and acid, e.g., sulfuric acid in acetone, aqueous acetic acid or aqueous hydrochloric acid in dioxane, undergo acid hydrolysis to form indenones of the formula

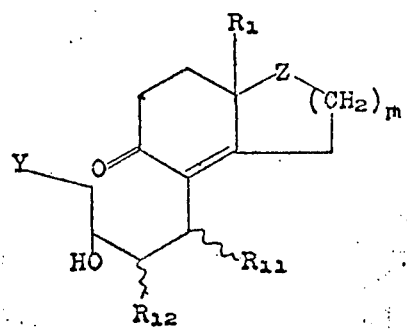

Ia' wherein $R_1$, $R_{11}$, $R_{12}$, Y and m have the same meaning as above.

The indenones of formula Ia' are themselves convertible to compounds of formula Ia via dehydration, for example, via acid catalyzed azeotropic distillation in benzene. Suitable acid catalysts are p-toluenesulfonic acid, potassium bisulfate, boron trifluoride etherate and the like. This reversible hydrolysis of compounds of formula Ia is useful in their preparation and purification. Thus, in instances where the direct purification of compounds of formula Ia is difficult it is often more facile to hydrolyze the compound of formula Ia to a compound of formula Ia', which can then be purified, for example, by chromatography, and subsequently be reconverted to the desired compound of formula Ia via dehydration.

The ketodienes of formula Ia-1 are readily converted to the corresponding 7β-alcohols and their esters as represented by the formula:

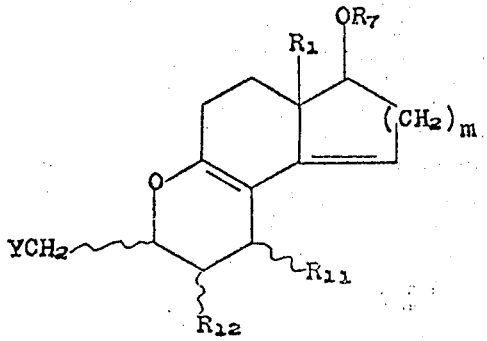

Ia-2 wherein Y, $R_1$, $R_7$, $R_{11}$, $R_{12}$ and m are as previously defined,
by the sequence of reactions comprising reduction of the ketone to the alcohol and, if desired, subsequent esterification.

The reduction can be effected by any of the known methods for the chemical reduction of a ketone, e.g., by reaction of dienone (Ia-1) with an alkali metal or Group III-metal reducing agent. By the term "alkali metal," as employed herein, is meant a Group I-metal having an atomic number of from 3 to 19, inclusive, i.e., lithium, sodium, and potassium. Group III-metals include those having atomic numbers of from 5 to 13, inclusive, i.e., boron and aluminum. Illustrative examples of these reducing agents include an alkali metal, preferably lithium or sodium, in liquid ammonia or a liquid aliphatic amine; tri(lower alkoxy)-aluminum compounds such as triisopropoxyaluminum; di(lower alkyl)-aluminum hydrides such as diethylaluminum hydride and diisobutyl-aluminum hydride; alkali metal-Group III-metal complex hydrides such as lithium aluminum hydride, sodium aluminum hydride, and sodium borohydride tri(lower alkoxy)alkali metal-Group III-metal complex hydrides such as trimethoxy lithium aluminum hydride and tributoxy lithium aluminum hydride; diisobutyl aluminum hydride and the like. The alkali metal-Group III-metal complex hydrides are preferred as reducing agents, with the nonalkaline reagents, such as lithium aluminum hydride, being especially preferred.

This reaction is effected in any suitable inert reaction medium, such s hydrocarbons, e.g., cyclohexane, benzene, toluene, and xylene; ethers, e.g., diethyl ether, diisopropyl ether, and tetrahydrofuran. Protic solvents, such as water or alcohols, should not be employed when lithium aluminum hydride is the reducing agent, but can be employed with sodium borohydride.

The remaining reaction conditions are not narrowly critical, although it is generally preferred to effect the reduction at reduced temperatures, i.e., below about room temperature (about 20°–25°C.). Temperatures in the range of from about 0°C. to about room temperature are normally employed.

The free alcohol is recovered from the reaction mixture after treatment of the mixture with acid. The alcohol can be esterified in known manner, for example, by base-catalyzed reaction with a carboxylic acid halide or carboxylic acid anhydride. Illustrative bases include inorganic bases such as sodium hydroxide and potassium hydroxide and organic bases such as a sodium alkoxy or an amine, especially a tertiary amine, and more particularly, pyridine and the picolines.

The ketodienes of formula Ia-1 can also be converted to their 7β-hydroxy-7α-hydrocarbyl derivatives represented by the formula:

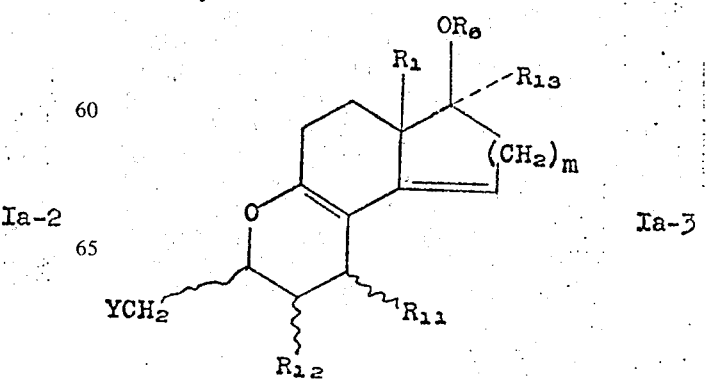

Ia-3 wherein Y, $R_1$, $R_6$, $R_{11}$, $R_{12}$ and m are as previously defined and $R_{13}$ is lower hydrocarbyl
by reaction of the ketodiene with a Grignard reagent of the formula:

$$R_{13}MgX \qquad \qquad VII$$

wherein $R_{13}$ is as previously defined and X is a halogen having an atomic number of from 17 to 35, inclusive (i.e., chlorine or bromine).

This Grignard reaction is conducted in known manner. For example, the Grignard reagent is prepared by reacting a hydrocarbyl halide with magnesium in an ether reaction medium, for example, ethyl ether or tetrahydrofuran, at elevated temperature, generally in the range of from about 40°C. to about 75°C. The ketodiene (Ia-1) is then added to the Grignard solution at about room temperature, although higher or lower temperatures can be employed. The resulting reaction product is hydrolyzed to produce the free alcohol, which can be esterified as discussed above.

Alternatively, the alcohols can be prepared by reaction of ketodiene (Ia-1) with a hydrocarbyl alkali metal compound such as methyl lithium, sodium acetylide, potassium acetylide, and the like.

The second step of the general synthesis of the tricyclic compounds of this invention comprises conversion of the dienes of formula Ia to the monoenes of formula Ib by catalytic hydrogenation. Suitable catalysts include the noble metals, such as platinum, palladium, rhodium, and the like, as well as Raney nickel and other hydrogenation catalysts. These catalysts can be employed in the form of the metal alone, or can be deposited on suitable support materials, such as carbon, alumina, calcium carbonate, barium sulfate, and the like. Palladium and rhodium are preferred as catalysts. The hydrogenation is preferably conducted in the presence of inert solvents such as hydrocarbons, alcohols, ethers, and the like. The reaction conditions of pressure and temperature are not narrowly critical, and normally a hydrogen pressure of about one atmosphere and a temperature of about room temperature are employed. These ambient conditions are generally preferred to avoid significant hydrogenation of the 4a,9b(10b)-double bond, although more severe conditions, for example, up to about 100°C. and up to about 100 atmospheres, can be employed if desired. The hydrogenation medium can be acidic, neutral, or basic, as may be desired, although neutral media, such as hydrocarbons, e.g., toluene or hexane, or basic media, such as an alcohol-base, e.g., methanol-sodium hydroxide, mixture are preferred for best results. In general, hydrogeantion of the diene of formula Ia leads to the corresponding monoene of formula Ib. However, in the event $R_8$ is an unsaturated hydrocarbyl radical, the hydrogenation, in addition to hydrogenating the ring double bond, also hydrogenates the 7α-hydrocarbyl substituent, converting it to an alkyl group.

Via the aforesaid catalytic hydrogenation C/D-trans compounds are formed in a major proportion when hydrogenating a diene of formula Ia-2. This method thus provides an advantageous synthesis of C/D-trans steroidal materials. When hydrogenating a diene of formula Ia-1, C/D-cis compounds are formed in a major proportion. This method thus provides an advantageous synthesis of C/D-cis steroidal materials.

Compounds wherein Z is carbonyl, as represented by the formula:

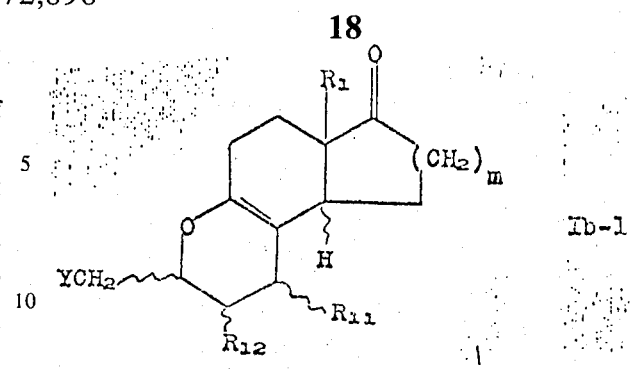

Ib-1 wherein Y, $R_1$, $R_{11}$, $R_{12}$ and m are as previously defined,
can be converted to the corresponding alcohols or esters of the formula:

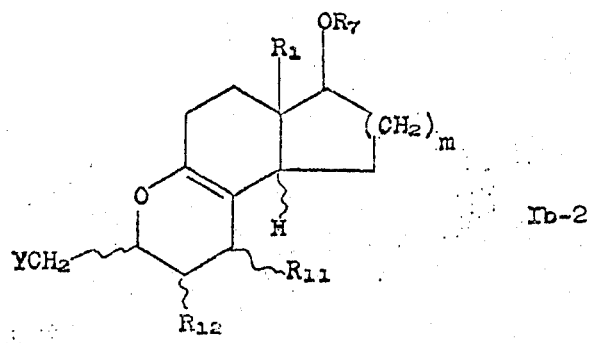

Ib-2 wherein Y, $R_1$, $R_7$, $R_{11}$, $R_{12}$ and m are as previously defined,
or to the 7β-hydroxy-7α-hydrocarbyl compounds of the formula:

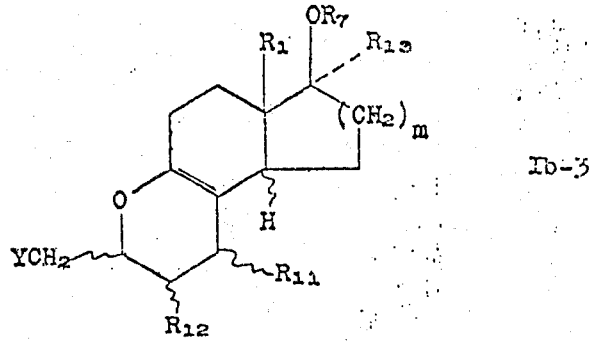

Ib-3 wherein Y, $R_1$, $R_7$, $R_{11}$, $R_{12}$, $R_{13}$ and m are as previously defined,
by the techniques discussed above regarding the dienes of formula Ia.

When Z is carbonyl and the hydrogenation is effected under basic conditions, there is a tendency toward the production of predominantly the 6a/9a(10a)-cis-compound; that is, the hydrogen atom in the 9a(10a)-position of formula Ib-1 is predominantly in the β-orientation. When these compounds are intended as intermediates for the synthesis of steroids having the C/D-trans-orientation, this technique is not particularly desirable. Although the ratio of β- to α-orientation falls to about 1:1 at neutral conditions when hydrogenating a compound wherein Z is carbonyl, it is preferred to hydrogenate a 7β-alcohol or ester of formula Ia-2 because the products of this hydrogenation are predominantly the 6a/9a(10a)-trans-compounds. Compounds of formula Ia-3 when subjected to the hydrogenation yield a ratio of β- to α-orientation in between that of the compounds of formula Ia-1 and that of the compounds of formula Ia-2. When monoenes of formula Ib-1 having C/D-trans configuration are desired, it is preferable to first reduce the dienone of formula Ia-1 to a corresponding hydroxy compound of formula Ia-2 prior to the catalytic hydrogenation. Following the catalytic hydrogenation the carbonyl moiety in formula Ib-1 can be regenerated by conventional means, such as oxidation with $CrO_3$.

The monoene compounds of formula Ib prepared by the above-described hydrogenation contain at least three asymmetric centers at positions 3, 6a and 9a when $m$ is one and at positions 3, 6a and 10a when $m$ is two. With respect to these three centers there are thus eight antipodal configurations possible. By virtue of the unique asymmetric induction of this invention, proceeding from a racemic starting material of formula II, IIa or IIb only four of these antipodes of formula Ib are prepared and proceeding from an optically active starting material of formula II, IIa or IIb only two of these antipodes of formula Ib are prepared. Moreover, by the above-described hydrogenation of this invention and by appropriate selection of the 7-substituent in the diene of formula Ia subjected to the hydrogenation there can predominantly be prepared the desired 6a,-9a(10a)-trans-stereo configuration. Thus, the eventual obtention of the more desired 13β-C/D-trans-configuration in the ultimate steroidal products is rendered more facile by the stereoselective reactions provided by this invention.

The final reaction of applicant's general process for the compounds of this invention is the conversion of the monoene of formula Ib to the perhydro compound of formula Ic by reaction of the monoene with a compound having the formula:

$R_2OH$      VIII wherein $R_2$ is as previously defined.

That is, the monoene of formula Ib is reacted with water, a primary alcohol, or a carboxylic acid. This reaction is catalyzed by mineral or organic acids, for example, hydrochloric acid, phosphoric acid, sulfuric acid, para-toluenesulfonic acid, and the like. Sulfuric acid is the preferred acid catalyst, and water the preferred reactant. Although not necessary, it is desirable to conduct this reaction in the presence of an added solvent, particularly in the event the compound of formula VIII is water. In this case, it is desirable to employ a solvent which is both miscible with water and a solvent for the monoene of formula Ib. Solvents of this nature include acetone, tert.-butanol, dioxane, and the like. The reaction temperature is not critical, and ambient temperature is normally employed, although higher and lower temperatures could be employed if desired.

As with the compounds of formulae Ia-1 and Ib-1, the compounds of general formula Ic wherein Z is carbonyl:

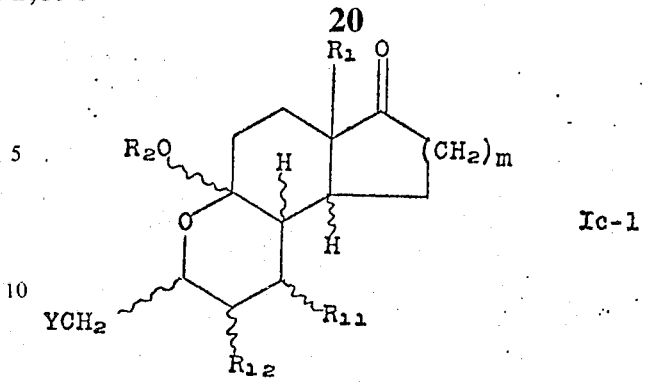

Ic-1 wherein Y, $R_1$, $R_2$, $R_{11}$, $R_{12}$ and $m$ are as previously defined
are readily converted to their corresponding alcohols:

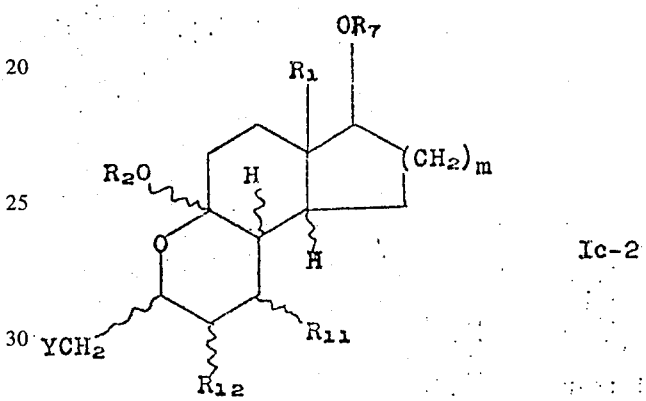

Ic-2 wherein Y, $R_1$, $R_2$, $R_7$, $R_{11}$, $R_{12}$ and $m$ are as previously defined,
or the β-hydroxy-α-hydrocarbyl compounds:

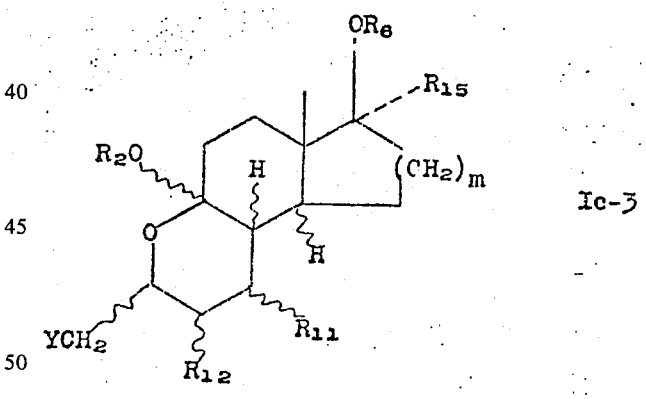

Ic-3 wherein Y, $R_1$, $R_2$, $R_6$, $R_{11}$, $R_{13}$ and $m$ are as previously defined,
by the previously described methods.

In a modification of the general technique outlined above, one can simultaneously effect the hydrogenation and hydration steps, for example, by hydrogenation of a diene of formula Ia in aqueous sulfuric acid. When this simultaneous hydrogenation-hydroation reaction is effected, it is preferred to begin with a diene having a hydroxyl group in the 7β-position.

As indicated above, the tricyclic compounds which form part of the present invention are useful as intermediates for the preparation of various steroid compounds, particularly 19-nor-steroids of the normal series, as illustrated by the following reaction scheme.

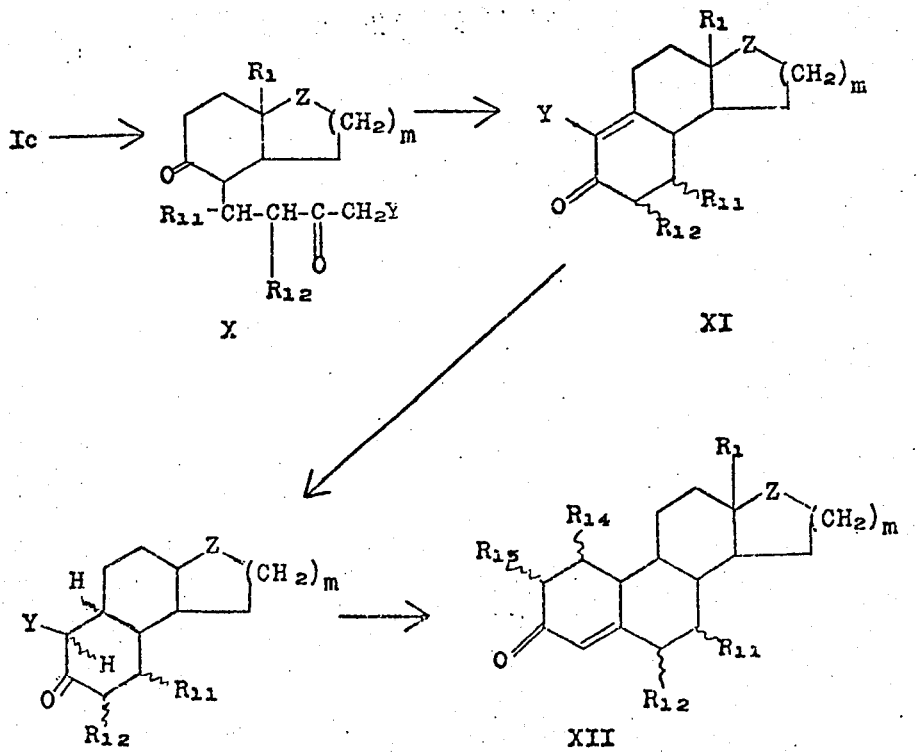

wherein $R_1$, $R_{11}$, $R_{12}$, $R_{14}$, $R_{15}$, Y, Z and m are as above.

In the first step of this reaction scheme, the compound of formula Ic is oxidized to form bicyclic compound of the formula X by contact with such oxidizing agents as chromic acid, potassium dichromate, or potassium permanganate. Jones reagent (chromic acid, sulfuric acid and acetone), or a chromic acid-acetic acid mixture are preferred as oxidizing agents. The nature of Z is unchanged in this reaction, except when Z is hydroxymethylene [—CH(OH)—]. In this instance, unless the hydroxyl group is protected, as by formation of a lower acyl ester, it is oxidized to form a carbonyl group. A hydroxylated product is readily obtained, however, by hydrolysis of a product ester. The reaction temperature is not narrowly critical, and temperatures in the range of from 0°C. to about 75°C. are suitable, although ambient temperatures are preferred.

In the second step, bicyclic compound (X) is treated with acid or base to effect cyclization to (XI). In this reaction, it is preferred that the water of reaction be removed, as by refluxing the reaction mixture with an azeotroping agent in the presence of a strong acid and separating the water from the condensate. Suitable strong acids are sulfuric acid, p-toluenesulfonic acid, potassium bisulfate and the like. Alternatively, base catalyzed dehydration can be utilized, for example, by refluxing compound (X) in the presence of methanolic sodium hydroxide.

The hydrogenation of cyclo-olefin XI is preferably effected with a noble metal catalyst, e.g., a palladium-charcoal catalyst or a rhodium catalyst. Mild conditions are generally employed, e.g., room temperature and atmospheric pressure are convenient conditions for this reaction. The hydrogenated compound of formula XIa is converted to the desired 19-nor-steroid of formula XII by heating it, preferably at reflux, with dilute aqueous acid, preferably a mineral acid such as hydrochloric acid in a lower alkanol solvent medium, preferably methanol.

Compounds of formula XI wherein Z is carbonyl can be converted into corresponding pregnane compounds i.e., compounds in which Z is of the formula

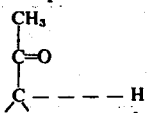

by known procedures. Thus, for example, 19-nor-14β-androst-4-ene-3,17-dione can be converted into 19-nor-14β,17α-progesterone. These procedures for converting androst-17-ones into pregnanes are best effected if all carbonyl groups other than that in the 17-position are initially protected.

As has been pointed out above, the products of this invention are produced in the form of various optically active antipodes which can be carried through the entire reaction sequence, or which can be resolved at suitable places during the reaction sequence. For example, at any stage wherein a compound having a secondary hydroxyl group is present, such as hydroxytetrahydropyran (IV), or any of the hydroxy compounds of formula I, one can react the secondary alcohol with a dicarboxylic acid to form a half-ester. Suitable dicarboxylic acids include lower alkyl dicarboxylic acids such as oxalic acid, malonic acid, succinic acid, glutamic acid, adipic acid, or aromatic carboxylic acids such as phthalic acid. The resulting half-ester is then reacted with an optically active base, such as brucine, ephedrine, or quinine, to produce a diastereomeric salt. The salts, after separation, are then readily reconverted to optically active alcohols. As an alternative, the secondary alcohol can be reacted with an optically active acid, for example, camphorsulfonic acid. The resulting diastereomeric esters are then separated and reconverted to the alcohols.

It is preferred that the resolution be effected at some stage in the synthesis of alken-3-one, as by the above-mentioned resolution of hydroxytetrahydropyran (IV). In a more preferred technique optically active 5-alkyl-5-valerolactone is obtained from 5-alkyl-5-oxopentanoic acid via known microbiological processes. The S-form of this lactone is the preferred form for use in accordance with this invention. In a third method, the racemic lactone can be hydrolyzed to the corresponding hydroxy acid, which is then resolved by treatment with an optically active base in the manner described above. Still other methods will be apparent to those skilled in the art. Resolution at such early stages in the overall process described herein is highly preferred because of the improved efficiency in the production of steroids having a desired stereo-configuration. Because the stereo-configuration is retained throughout the synthesis of alken-3-one (II), and further because the condensation of alken-3-one or variant (II, IIa or IIb with cycloalkanedione (III) is stereo-specific, one, by proper selection of stereo-isomers at these early stages, can ensure that substantially all of the tricyclic compounds of this invention and the steroids derived therefrom have a selected stereo-configuration. Thus, by this technique, the production of compounds of the undesired configuration is minimized or prevented entirely, with an attendant increase in the efficiency of the production of compounds of the desired configuration.

In the claims, all compounds shall be construed to include, independently, the racemic form of the compound and independently, each enantiomeric form, i.e., the $d$ and $l$ configurations unless specifically indicated otherwise.

The following examples are illustrative. All temperatures are in degree Centigrade and all products having centers of asymmetry are racemic unless specifically indicated otherwise.

EXAMPLE 1

(±)-9,9-Ethylenedioxy-5-hydroxy-decanoic acid lactone

25 G. of the hemiacetal, (±)-6-[3-(2-methyl-1,3-dioxolan-2-yl)propyl] tetrahydropyran-2-ol was dissolved in a mixture of dimethylformamide (DMF) acetic acid- water-sodium acetate (anhydrous) (250 ml; 120 ml. H$_2$O/120 ml DMF/40 ml AcOH/24 g. NaOAc). Bromine (7 ml.) was then added to the cold (5°–10°) solution over 2–5 min. and the mixture was then stirred for a further 45 min. at room temperature. Aqueous sodium bisulphite solution and brine were then added and the organic products were isolated with benzene (5 × 125 ml.). The benzene extracts were washed with saturated brine solution (5 × 50 ml.) and then taken to dryness in vacuo. The crude lactone, (±)-9,9-ethylenedioxy-5-hydroxy-decanoic acid lactone yielded pure material on distillation bp 138–140/.02 mm.

In another experiment the hemiacetal, (±)-6-[3-(2-methyl-1,3-dioxolan-2-yl)propyl] tetrahydropyran-2-ol gave the lactone, (±)-9,9-ethylenedioxy-5-hydroxy-decanoic acid lactone, b.p. 141°–145°/.3 mm.

The starting material may be prepared as follows.

A solution of 2,2-ethylenedioxy-5-chloropentane in tetrahydrofuran (THF) (50 ml; 164 g. in 1600 ml. THF) was added to magnesium (38 g.) activated with a crystal of iodine. This mixture was stirred and heated at reflux until the reaction commenced. The rest of the chloroketal solution was then added over approximately 1 hr. to sustain gentle reflux. After complete addition, the mixture was stirred at room temperature for a further 2 hr.

A solution of freshly distilled glutaraldehyde (110 g.) in THF (1000 ml.) cooled to −40° was treated with the above Grignard reagent (as rapidly as possible) and then stirred 30 min at −30° and a further 1 hr. at 0°. Aqueous ammonia chloride solution (300 ml; 25 percent) was then added and the products were isolated with ether. Removal of the solvents in vacuo gave the product as a mobile liquid (185 g.). This material was stirred at 50° with aqueous sodium sulfite solution (1500 ml; 20 percent) and the pH was adjusted first to pH 6.5 with acetic acid and then pH 7.5 with sodium hydroxide solution (20 percent). The aqueous phase after stirring for 1 hr. at 50° was extracted with ether and then treated with caustic soda solution (20 percent) to pH 12. Extraction with benzene then furnished the hemiacetal (±)-6-[3-(2-methyl-1,3 -dioxolan-2-yl)propyl]tetrahydropyran-2-ol (118 g.) as a mobile, pale yellow liquid. A sample was distilled (molecular still) to give a colorless product, b.p. 130°–132°/.1 mm.

EXAMPLE 2

(±)-9-Oxo-5-hydroxydecanoic acid lactone 52.4 G. of the ketal lactone, (±)-9,9-ethylenedioxy-5-hydroxy-decanoic acid lactone dissolved in acetone (150 ml.) was treated with water (75 ml.), dilute aqueous sulphuric acid (2N; 45 ml.) and left to stand at room temperature for 16 hr. Addition of brine and extraction with benzene gave the crude lactone, (±)-9-oxo-5-hydroxydecanoic acid lactone which on distillation yielded pure material >98 percent pure by vpc bp 134°/.05 mm.

EXAMPLE 3

(±)-9,9-Phenylenedioxy-5-hydroxy-decanoic acid lactone

15 G of a solution of the ketolactone (±)-9-oxo-5-hydroxydecanoic acid lactone in benzene (300 ml.) was treated with 20 g. catechol and 0.6 g. p-toluenesulphonic acid (PTS). The mixture was heated at reflux under nitrogen in conjunction with a soxhlet extraction apparatus equipped with a thimble filled with calcium hydride. After 18 hr. at reflux the mixture was cooled and chromatographed directly on silica gel (.2–.5 mm mesh; 650 g.). Elution with 5%, 10% and 15% ethyl acetate-benzene mixtures yielded the ketal ester.

Distillation of the above material gave catechol and the desired lactone, (±)-9,9-phenylenedioxy-5-hydroxy-decanoic acid lactone, bp 152°–170°/.2 mm. (This was a short path distillation and the majority of the material had bp 157°–162°). A sample of this material was redistilled (Kugel Rhor) and gave material, bp 140°–54°/.02 mm.

EXAMPLE 4

(±)-6-(4,4-Phenylenedioxypentyl)-2-(2-diethylaminoethyl)-tetrahydropyran-2-ol 1.6 G. of the ketal lactone, (±)-9,9-phenylenedioxy-5-hydroxy-decanoic acid lactone in tetrahydrofuran (THF; 15 ml.) was cooled to −45° and treated over 5 min. with a solution of vinyl magnesium chloride in THF (4.6 ml; 2 mol/liter). After stirring a further 25 min. at −45°, methanol (5 ml.) was added followed by an aqueous ammonium chloride solution (15 percent; 20 ml.). The products were extracted into ether and the ether extracts then treated with diethylamine (5 ml.) and dried over magnesium sulphate. Removal of the solvents in vacuo gave the crude Mannich base which was separated from neutral material with dilute aqueous acid (1N.$H_2SO_4$; 4 × 15 ml.). The aqueous extracts were made basic with caustic potash solution and the products isolated with ether. Removal of the solvents in vacuo gave the Mannich base, (±)-6-(4,4-phenylenedioxypentyl)-2-(2-diethylaminoethyl)-tetrahydropyran-2-ol as a mobile liquid.

This material showed one spot on tlc analysis on development with a benzene/triethylamine (9:1) system.

EXAMPLE 5

(±)-3-(4,4-Phenylenedioxypentyl)-6a,β-methyl-1,2,3,5,6,6a-hexahydrocyclopenta[f][1]benzopyran-7(8H)-one 10.6 G. of the Mannich base, (±)-6-(4,4-phenylenedioxypentyl)-2-(2-diethylaminoethyl)-tetrahydropyran-2-ol in toluene (80 ml.) was added rapidly to a refluxing solution of 2-methylcyclopentan-1,3-dione (4.7 g.) in toluene (50 ml.), acetic acid (23.2 ml.) and pyridine (7.2 ml.) under nitrogen. After heating at reflux for a total of 4 hr. (reaction followed by tlc) the mixture was cooled, diluted with toluene (100 ml.) and extracted with water (4 × 50 ml.), saturated aqueous sodium bicarbonate solution (1 × 50 ml.), brine (1 × 50 ml.) and dried over $MgSO_4$. Removal of the solvents in vacuo yielded the crude crystalline dienolether, (±)-3-(4,4-phenylenedioxypentyl 6a,β-methyl-1,2,3,5,6,6a-hexahydrocyclopenta[f][1]benzopyran-7(8H) one, m.p. 115°–120°. A sample of this material was recrystallized from benzene-hexane mixture to give pure material mp 126°–129°.

EXAMPLE 6

(±)-3-(4,4-Phenylenedioxypentyl)-6a,β-methyl-1,2,3,5,6,6a,7,8-octahydrocyclopenta[f][1]benzopyran-7β-ol 10.7 G. of the crude dienolether, (±)-3-(4,4-phenylenedioxypentyl)-6a,β-methyl-1,2,3,5,6,6a-hexahydrocyclopenta[f][1]benzopyran-7(8H)-one dissolved in THF/ether (100 ml; 1:1) was added to a slurry of lithium aluminum hydride (4 g.) in a THF/ether mixture (400 ml; 1:1) cooled in an ice-salt bath (temp. held at ~3°). After complete addition the mixture was stirred for a further 10 min. at −5° and 1¾ hr. at room temperature (followed by tlc). Wet ether (100 ml.) was then added followed by a saturated aqueous solution of sodium sulphate (25 ml.). The coagulate salts were then filtered off, washed with THF and the filtrate was dried over MgSO. Removal of the solvents in vacuo gave the crude alcohol, (±)-3-(4,4-phenylenedioxypentyl)-6a,β-methyl-1,2,3,5,6,6a,7,8-octahydrocyclopenta[f][1]benzopyran-7β-ol.

EXAMPLE 7

(±)-3-(4,4-Phenylenedioxypentyl)-6a,β-methyl-1,2,3,5,6,6a,7,8,9,9a-decahydrocyclopenta[f][1]benzopyran-7β -ol 11.2 G. of the crude dienolether alcohol, (±)-3-(4,4-phenylenedioxypentyl)-6a,β-methyl-1,2,3,5,6,6a,7,8-octahydrocyclopenta[f][1]benzopyran-7β-ol (this still contains some solvent) was dissolved in toluene (100 ml.) treated with 2 g. of a 5% Pd/C catalyst and hydrogenated at room temperature and pressure. After 5½ hr. the uptake of hydrogen stopped (635 ml; theory 700 ml. at room temperature and pressure for 10.7 g.) and the solids were filtered off and washed with toluene. Removal of the solvents in vacuo gave the enol ether, (±)-3-(4,4-phenylenedioxypentyl)-6a,β-methyl-1,2,3,5,6,6a,7,8,9,9a-decahydrocyclopenta[f][1]benzopyran-7β-ol, as an oil.

EXAMPLE 8

(±)-4-(3-Oxo-7,7-phenylenedioxyoctyl)-1a,β-methyl-perhydroindan-1,5-dione 10.76 G. of the crude enol ether, (±)-3-(4,4-phenylenedioxypentyl)-6a,β-methyl-1,2,3,5,6,6a,7,8,9,9a-decahydrocyclopenta[f][1]benzopyran-7β-ol dissolved in acetone (210 ml.) was treated with aqueous sulphuric acid solution (50 ml; 0.5N) and left at room temperature for 2 hr. (followed by tlc). Dilution with ether (500 ml.) and washing with brine (5 × 100 ml.) and saturated aqueous sodium bicarbonate solution (1 × 50 ml.) [all aqueous extracts were backwashed with ether (1 × 100 l.)] gave the hemiketal, (±)-3-(4,4-phenylenedioxypentyl)-6aβ-methyl-4-hydroxyperhydrocyclopenta[f][1]benzopyran-7β-ol as a glass.

This material was virtually pure by tlc and showed no enol ether band in the ir. The strong hydroxyl bands at 3450 and 3757 cm. and the characteristic catechol-ketal bands were most pronounced. 10.37 G. of this crude hydration product, was dissolved in acetone (200 ml.) cooled in an ice bath and treated at 0°–5° with fresh Jones[(5)] chromic acid mixture (20 ml.) over 10 min. After stirring a further 1½ hr. at room temperature, aqueous sodium bisulphite solution (100 ml; 10%) and brine (100 ml.) were added and the organic materials were isolated with benzene (4 × 200 ml.). The benzene extract was washed with brine and aqueous sodium carbonate solution (10%) to give the neutral triketone, (±)-4-(3-oxo-7,7-phenylenedioxyoctyl)-1a,β-methyl-perhydroindan-1,5-dione as a pale yellow liquid. This material showed one major spot on tlc and had bands in the ir spectrum (film) at 1730 $cm^{-1}$ (cyclopentanone, 1705 $cm^{-1}$ (saturated carbonyl) and 1480, 1240 and 730 $cm^{-1}$ (catechol ketal).

EXAMPLE 9

(±)-6-(3,3-Phenylenedioxybutyl)-3a,β-methyl-4,5,8,9,9a,9b-hexahydro-1H-benz[e]indene-3,7(2H,8H)-dione 8.6 G. of a solution of the crude triketone, (±)-4-(3-oxo-7,7-phenylenedioxyoctyl)-1a,β-methyl-perhydroindan-1,5-dione in methanol (250 ml.) containing 1 g. of potassium hydroxide was heated at reflux, under nitrogen, for 1 hr. (followed by ir). Benzene (500 ml.) was added and the mixture was extracted with dilute aqueous sulphuric acid (3 × 50 ml 0.5N), saturated sodium bicarbonate solution (1 × 100 ml.), brine and then dried over $MgSO_4$ (note: all aqueous extracts were backwashed with benzene). Removal of the solvents in vacuo furnished the crude tricyclic material, (±)-6-(3,3-phenylenedioxybutyl)-3a,β-methyl-4,5,8,9,9a,9b-hexahydro-1H-benz[e]indene-3,7(2H,8H)-dione as a semi-solid. This material was digested with ethanol (50 ml.) to give the crystalline material, mp 166°–170°.

A sample of this material was recrystallized from ethanol to yield pure colorless crystals, m.p. 173°–175°.

EXAMPLE 10

(±)-19-Nor-androst-4-ene-3,17-dione 4.01 G. of crude (±)-6-(3,3-phenylenedioxybutyl)-3a,β-methyl-4,5,8,9,9a,9b-hexahydro-1H-benz[e]indene-3,7(2H,8H)-dione was dissolved in THF (45 ml.) containing triethylamine (.8 ml.) and 400 mg. of a 5 percent Pd/C catalyst and hydrogenated at room temperature and pressure. After 6 hr., the uptake of hydrogen ceased (280 ml. consumed; theory 285 ml/RTP). The solids were filtered off, washed with THF and the filtrate was taken to dryness in vacuo. The crude hydrogenation product (±)-6-(3,3-phenylenedioxybutyl)-3a,β-methyl-4,5,5a,6,8,9,9a,9b-octahydro-1H-benz[e]indene-3,7-(2H,8H)-dione (some solvent residue) showed bands in the ir spectrum (film) at 1705 cm$^{-1}$ (cyclohexanone), 1735 cm$^{-1}$ (cyclopentanone) and 1480, 1240 and 740 cm$^{-1}$ (catechol ketal) and was virtually one spot material on tlc. 4.3 G. of this crude hydrogenation material was dissolved in methanol (70 ml.) and 35 ml. of 4N HCl and the solution was heated at reflux for 6 hr. (followed by tlc and ir). The mixture was cooled, treated with benzene (200 ml.) and extracted with aqueous caustic soda solution (1N; 3 × 100 ml.) and brine (2 × 50 ml.). (All aqueous extracts were backwashed with benzene). Removal of the solvents in vacuo gave crude 19-nor-androst-4-en-3,17-dione which on crystallization from dichloromethane/isopropyl ether mixture yielded pure (±)-19-nor-androst-4-ene-3,17-dione, m.p. 155°–157°, identical in all respects with authentic (±)-19-nor-androst-4-ene-3,17-dione, mp. mx mp. tlc, ir, and uv.

EXAMPLE 11

(±)
3-(4,4-Phenylenedioxypentyl)-6a,β-ethyl-1,2,3,5,6,6a-hexahydrocyclopenta[f][1]benzopyran-7(8H)-one (±) 2-(2-diethylaminoethyl)-6-(4,4-phenylenedioxypentyl)tetrahydropyran-2-ol (3.8 g.) in toluene (20 ml.) was added to a refluxing solution of 2-ethylcyclopentan-1,3-dione (2 g.) in toluene (40 ml.) and acetic acid (20 ml.) and heated at reflux for 1 hour.

Isolation of the organic materials with toluene gave pure (±) 3-(4,4-phenylenedioxypentyl)-6a,β-ethyl-1,2,3,5,6,6a-hexahydrocyclopenta[f][1]benzopyran-7(8H)-one (2.95 g.) after chromatography on alumina. Uv. (EtOH) λmax 252 mμ. (εmax $^{16,000}$) Calcd. for $C_{25}H_{30}O_4$: C, 76.11; H, 7.67; Found C, 75.68; H, 7.83.

EXAMPLE 12

(±)
6-(3,3-phenylenedioxybutyl)-3a,β-ethyl-4,5,8,9,9a,9b-hexahydro-1H-benz[e]inden-3,7-(2H,3aH)-dione Crude (±) 3-(4,4-phenylenedioxypentyl)-6a,β-ethyl-1,2,3,5,6,6a-hexahydrocyclopenta[f][1]benzopyran-7(8H)-one (47 g.) dissolved in tetrahydrofuran (200 ml.) was added to a cold (−10°) slurry of lithium aluminum hydride (6 g.) in tetrahydrofuran (200 ml).

After stirring for 2 hours at room temperature, saturated aqueous sodium sulfate solution was added (40 ml.) and the solids were filtered off.

Removal of the solvents in vacuo gave racemic 3-(4,4-phenylenedioxypentyl)-6a,β-ethyl-1,2,3,5,6,6a,7,8-octahydrocyclopenta[f][1]benzopyran-7β-ol as an oil (51 g.). Ir.(film) 3400(OH); 1640 dienol ether); 1450,1240 and 730 cm$^{-1}$ catechol ketal.

The above crude material was dissolved in toluene, treated with Pd/C (5%; 5 g.) and hydrogenated at room temperature and pressure until the hydrogen uptake stopped (approximately 30 hours).

The solids were filtered off and the solvents removed in vacuo to yield crude (±) trans-3-(4,4-phenylenedioxypentyl)-6a,β-ethyl-1,2,3,5,6,6a,7,8,9,9a-decahydrocyclopenta[f][1]-benzopyran-7β-ol as an oil (48 g.). Ir. (CHCl$_3$) 3425 and 3580(OH) 1480 cm$^{-1}$ (catechol ketal).

The above material was dissolved in acetone (500 ml.) treated with dilute aqueous sulfuric acid (0.5 N; 50 ml.) and left to stand at room temperature for 2 hours. The solution was then cooled to 5° and treated over 30 minutes with fresh Jones chromic acid reagent (125 ml.). The mixture was then stirred for a further 2 hours at room temperature and then quenched with aqueous sodium bisulfite solution (20%; 50 ml.).

Isolation of the organic materials with benzene and extration with aqueous sodium carbonate solution gave racemic trans-4-(3-oxo-7,7-phenylenedioxyoctyl)-1a,β-ethyl-perhydroindane-1,5-dione (34.4 g.) after removal of the organic solvents in vacuo. I.R. (Film) 1735 (cyclopentanone); 1708 (cyclohexanone and straight chain ketone); 1480; 1275 and 740 cm$^{-1}$ (catechol ketal).

The crude bicyclic material (34.4 g.) was dissolved in methanol (110 ml.) and added to a reflux solution of potassium hydroxide (3.5 g.) in methanol (200 ml.).

After 1 hour at reflux the organic materials were isolated with benzene and chromatography on silica gel (800 g.) gave racemic 6-(3,3-phenylenedioxybutyl)-3a,β-ethyl-4,5,8,9,9a,9b-hexahydro-1H-benz[e]inden-3,7-(2H,3aH)-dione (20 g.) as an oil. I.R. (CHCl$_3$) 1735 (cyclopentanone); 1663 and 1600 (cyclohexanone); 1480 cm$^{-1}$ (catechol ketal).

EXAMPLE 13

(±)-13β-ethylgon-4-en-3,17-dione

Racemic 6-(3,3-phenylenedioxybutyl)-3a,β-ethyl-4,5,8,9,9a,9b-hexahydro-1H-benz[e]inden-3,7-(2H,3aH)-dione (20 g.) was dissolved in ethanol (250 ml.) containing triethylamine (2 ml.) and Pd/C (5%; 4g.) and hydrogenated at room temperature and pressure until the uptake of hydrogen stopped to yield 6-(3,3-phenylenedioxy)-3a,β-ethyl-4,5,5a,6,8,9,9a,9b-octahydro-1H-benz[e]indene-3,7-(2H,8H)-dione in solution.

The solids were filtered off and dilute aqueous hydrochloric acid (4N; 200 ml.) was added and the mixture was heated at reflux for 5 hours.

The organic materials were isolated with benzene and the benzene extract was then washed free of catechol with dilute aqueous caustic soda solution.

Removal of the solvents in vacuo yielded a semisolid which on crystallization from dichloromethane-isopropyl ether mixture yielded pure racemic 13β-ethylgon-4-en-3,17-dione (6.3 g.) m.p. 159°–161°.

EXAMPLE 14

2R,6S-2[2-(R-α-phenethylamino)ethyl]-6-(4,4-phenylenedioxypentyl) tetrahydropyran-2-ol and 2S,6R-2[2-R-α-phenethylamino)ethyl]-6-(4,4-phenylenedioxypentyl) tetrahydropyran-2-ol (±) 9,9-Phenylenedioxy-5-hydroxy decanoic acid lactone (11.1 g.) dissolved in tetrahydrofuran (100 ml.) at −50° was treated with vinylmagnesium chloride solution (39 ml.; 2 molar in T.H.F.) over 3 minutes. The mixture was then stirred at −45° for 25 minutes, quenched with methanol (10 ml.) and ammonium chloride solution (15%; 100 ml.) and extracted with ether.

Removal of the solvents in vacuo gave the crude vinyl ketone as an oil. This material was dissolved in benzene (20 ml.) and treated with a solution of α-phenethylamine (3.9 g.) in benzene (20 ml.) and left at room temperature for 3 hours.

The solvents were removed in vacuo and the residue extracted with hexane. This hexane extract was filtered through alumina (50 g.) to give the mixture of diastereomeric bases (11 g.) as a liquid.

This material was dissolved in hexane and left to crystallize. Recrystallization yielded the pure 2S,6R,2-[2-(R-α-phenethylamino)ethyl]6-(4,4-phenylenedioxypentyl)-tetrahydropyran-2-ol, m.p. 72°–76°; $[\alpha_D]=+37°$ (c = 5, benzene).

The mother liquors from the first crystallization were taken to dryness and dissolved in acetone (25 ml.). This solution was added to oxalic acid (2 g.) in acetone (30 ml.) and left to crystallize.

Recrystallization of the solids from acetone yielded pure 2R,6S,2-[2-(R-α-phenethylamino)ethyl]-6-(4,4-phenylenedioxypentyl) tetrahydropyran-2-ol oxalate, m. p. 80°; $[\alpha_D] = +21°$ (c = 1.248, methanol).

EXAMPLE 15

3S,6aS,3-(4,4-phenylenedioxypentyl)-6a,β-methyl-1,2,3,5,6,6a-hexahydrocyclopenta[f][1]benzopyran-7(8H)-one 2S,6R-2[2-(R-α-phenethylamino)ethyl]-6-(4,4-phenylenedioxypentyl) tetrahydropyran-2-ol (1.25 g.) in toluene (45 ml.) and aqueous acetic acid (18 ml.; 95%) was treated with pyridine (9 ml.) and 2-methylcyclopentane-1,3-dione (0.5 g.) and heated at 110° for 7 hours. After this time the water was taken off with a Dean-Stark separator (~ 45 minutes) and the mixture cooled.

Isolation of the materials with benzene and chromatography on alumina yielded the dienol ether.

Crystallization from hexane gave optically pure 3S,6aS,3-(4,4-phenylenedioxypentyl)6a,β-methyl-1,2,3,5,6,6a-hexahydrocyclopenta[f][1]benzopyran-7(8H)-one, m.p. 109°–112°, $[\alpha_D] = -121°$ (c = 1.0, CHCl$_3$).

EXAMPLE 16

(±)-19-norandrost-4-en-3,17-dione 3R,6aS,3-(4,4-phenylenedioxypentyl)-6a,β-methyl-1,2,3,5,6,6a-hexahydrocyclopenta[f][1]benzopyran-7(8H)-one was converted in good yield into the above-captioned product having a melting point of 172° using the procedure of Examples 6, 7, 8, 9 and 10.

EXAMPLE 17

(±)-6-(4,4-Phenylenedioxypentyl)-tetrahydropyran-2-ol

Freshly distilled glutaraldehyde (100 g.) dissolved in dry THF (700 ml.) was cooled to −65° and treated rapidly with the cold (−20°) Grignard reagent over ~30 min. (the temperature was held at −60° → −50°C. with a dry ice acetone bath). The mixture was then allowed to warm up to room temperature (~1 hr.) and then stirred a further 90 min. at room temperature (Note: sometimes on warming to room temperature an exotherm sets in and cooling is required). The reaction mixture can be stored 16–24 hr. at 5° or worked up after 90 min. at room temperature.

To work up, the reaction mixture was cooled to 5° and treated with an aqueous solution of ammonium chloride (150 ml; 25 percent). The solids were filtered off, washed well with more THF and the THF was removed in vacuo to yield the crude hemiacetal (±)-6-(4,4-phenylenedioxypentyl)-tetrahydropyran-2-ol (270 g.). This material assayed for ~75 percent purity by chromatography or silica gel.

The starting material may be prepared as follows.

A. Preparation of the Grignard reagent

A total of 100 ml. of a solution of 2,2-phenylenedioxy-5-chloropentane in dry tetrahydrofuran obtained by adding 213 g. of the chloroketal to 1.4 l. of THF distilled from calcium hydride was added to 28 g. of magnesium turnings activated with iodine under nitrogen.

The mixture was then heated to 36°–38° for ~5 min. and then treated with dibromoethane (.5 ml.). In general, the reaction became mildly exothermic at this point and had to be cooled to maintain the temperature range of 36°–38°C. After stirring 15–20 min. more, the rest of the chloroketal solution was added over ~1 hr. Again cooling was required. After stirring a further 45–60 min. the exotherm subsided and the mixture was heated to 36°–38° for a further 2 hours after which time virtually no starting material remains.

The Grignard reagent can be stored under nitrogen at 5° for several days. The progress of the reaction was followed by vapor phase chromatography. Thus, an aliquot (0.5 ml.) of the reaction mixture was added to aqueous ammonium chloride solution (2 ml; 15 percent) and ether (0.5 ml.). The organic extract was then analyzed at 150°C. on an 8 foot × ¼ inch column with 3 percent SE 30 silicone on chom. w. (80–100) AW-DAKS.

B. Production of dry glutaraldehyde

Aqueous glutaraldehyde solution (1 l.; 50 percent Union Carbide) was treated with benzene (2 l.) cooled to 5° and dried with magnesium sulfate (700 g.) for 15 min. The solution was then heated at reflux for 1 hr. in conjunction with a Dean and Stark water separator. The solvents were then removed in vacuo (50° at 10 mm) and the residue distilled to give a center cut (315 g.) of dry glutaraldehyde, b.p. 80°–81°/~10 mm.

EXAMPLE 18

(±)-9,9-Phenylenedioxy-5-hydroxy-decanoic acid lactone a. A solution of sodium hydroxide (91 g.) in water (225 ml.) was added to silver nitrate (195 g.) dissolved in water (650 ml.) at room temperature and then the mixture was heated to 55°–60°. Methanol (1300 ml.)

was then added and the temperature fell to 45°. A solution of (±)-6-(4,4-phenylenedioxypentyl)-tetrahydropyran-2-ol (107.7 g. crude) in methanol (150 ml.) was then added over 10 min. The temperature rose to 53° and after the initial exotherm the mixture was heated; with stirring, under nitrogen for a further 1 hr. The solids were filtered off and washed well with a methanol-water mixture (1:1, 3 × 200 ml.). The filtrate was then extracted with toluene (500 ml.) acidified to pH 1 with aqueous sulfuric acid (6N) and extracted with dichloromethane (4 × 500 ml.). Removal of the solvents in vacuo yielded a mixture of the lactone and hydroxy acid (83 g.). This material was dissolved in benzene (500 ml.) and treated with p-toluenesulfonic acid (2 g.) in more benzene (100 ml.). After standing for 1 hr. at room temperature the mixture was washed with aqueous sodium bicarbonate solution and the organic solvents were removed in vacuo to yield virtually pure lactone (±)-9,9-phenylenedioxy-5-hydroxy-decanoic acid lactone (76 g.) (as estimated by tlc and ir).

b. The hemiacetal (±)-6-(4,4-phenylenedioxypentyl)-tetrahydropyran-2-ol (1.77 g.) in ethyl acetate (100 ml.) containing platinum black (922 mg.) was stirred at room temperature under an atmosphere of oxygen for 48 hr. The solids were filtered off and the product (±)-9,9-phenylenedioxy-5-hydroxy-decanoic acid lactone was isolated by distillation (1.5 g.).

c. The crude hemiacetal (±)-6-(4,4-phenylenedioxypentyl)tetrahydropyran-2-ol (233 g.) dissolved in toluene (1.2 l.) was added to a solution of sodium dichromate bishydrate (315 g.) in acetic acid (1.2 l.). The reaction mixture was held at 35° with cooling until no longer exothermic (~2 hrs.), and then stirred ~16 hrs. at room temperature. Water (2.5 l.) was added and the materials were isolated with toluene (4 × 500 ml.). The combined toluene extracts were washed with brine and distilled to give the lactone (±)-9,9-phenylenedioxy-5-hydroxy-decanoic acid lactone (125 g.) of moderate purity (~80 percent). A purer product was obtained when the toluene layer was washed first with aqueous sodium bicarbonate solution (44–46 percent yield vpc pure).

d. The crude hemiacetal (±)-6-(4,4-phenylenedioxypentyl)tetrahydropyran-2-ol (78 g.) in DMF (400 ml.) was added to a solution of bromine (30.5 ml.) in a buffer mixture (640 ml.) (420 ml. $H_2O$/480 DMF/160 ml. AcOH/160 g. NaOAc.$2H_2O$) at 0°–5°C.

After stirring 1 hr. at room temperature, aqueous sodium bisulfite was added (250 ml; 15 percent) and the organic materials were isolated with benzene. Removal of the solvents gave a brown colored oil which was dissolved in methanol (500 ml.) and treated with potassium hydroxide (30 g.) dissolved in water (300 ml.). After 30 min. at room temperature, water (500 ml.) was added and the mixture was extracted with ether. The aqueous phase was acidified and extracted with methylene chloride. Removal of the solvents "in vacuo" and distillation of the residue (oil jacketed flask at 0.3 mm) gave the lactone (±)-9,9-phenylenedioxy-5-hydroxy-decanoic acid lactone (29–33 g.). This material was contaminated by some aromatic-ring brominated material.

EXAMPLE 19

2S,6R-2-[2-(S-α-phenethylamino)ethyl]-6-(4,4-phenylenedioxypentyl)-tetrahydropyran-2-ol oxalate The lactone (±)-9,9-phenylenedioxy-5-hydroxy-decanoic acid lactone (118 g.) dissolved in THF (1 l.) was cooled to −70°C. under nitrogen. A solution of vinyl magnesium chloride (315 ml; 2.28 molar) in THF was added over 6 min. (temp. held between −50° and −70°) and the mixture was then stirred a further 14 min. at −50°. After this time the temperature was lowered to −65° and methanol (50 ml.) was added (3 min.) followed by aqueous ammonium chloride solution (500 ml; 10 percent). (The temperature rose to ~−5°).

The products were then isolated with ether (5 × 500 ml.) and dried with $MgSO_4$. The solids were filtered off and the filtrate was concentrated to ≈200 ml. in vacuo at 40°–45°. The concentrate was treated with benzene (250 ml.) and a solution of (S)-α-phenethylamine (51 g.) in benzene (150 ml.) and kept at room temperature overnight (3–4 hr. will suffice; slight cooling is initially required). The solvents were taken to dryness and the residue (193 g.) was extracted with boiling hexane (1 × 500 ml. and 2 × 250 ml.) and the combined hexane extracts were again taken to dryness in vacuo. The residue (157.2 g.) was dissolved in acetone (400 ml.) and added to a solution of oxalic acid (49 g.) in acetone (400 ml.) After standing 8 hr. at room temperature and 8 hr. at ≈5°, the solids were filtered off, washed with acetone (2 × 100 ml.) and dried over $P_2O_5$ at 0.5 mm. This solid (84.2 g.) had m.p. 78°–82°, $[\alpha]_D$ −21° (c = 6.45, methanol) and was recrystallized from methyl ethyl ketone (1.1 l.) (some insoluble solids were filtered off) and gave pure 2S,6R-2-[2-(S-α-phenethylamino)ethyl]-6-(4,4-phenylenedioxypentyl)-tetrahydropyran-2-ol oxalate (51.2 g.), m.p. 81°–83°, $\alpha_D$ −23.3° (c = 3.95, methanol).

Anal. Calcd for $C_{26}H_{35}NO_4(CO_2H)_2$: C, 65.23; H, 7.23; N, 2.72. Found: C, 64.91; H, 7.09; H, 2.49.

All the mother liquors were taken to dryness and the residue was partitioned between water (800 ml.) and hexane (400 ml.). The aqueous phase was re-extracted with hexane (400 ml.) and the combined hexane extracts were then washed with aqueous acetic acid (10 percent).

All the aqueous phases were combined and made basic with sodium carbonate solution (130 g. in 400 ml. $H_2O$). The organic materials were extracted into hexane and yielded an oily solid on concentration (75 g.). This material was recrystallized three times from hexane to give pure 2R,6S-2-[2-(S-α-phenethylamino)-ethyl]-6-(4,4-phenylenedioxypentyl)-tetrahydropyran-2-ol (40 g.), m.p. 78°–80°; $[\alpha]_D$ −37° (c = 3.42; benzene).

Anal. Calcd. for $C_{26}H_{35}NO_4$: C, 73.38; H, 8.29; N, 3.29. Found: C, 73.68; H, 8.40; N, 3.47.

All the above mother liquors were taken to dryness and dissolved in a mixture of acetone (100 ml.) and dilute aqueous sulfuric acid (1N; 100 ml.) and left to stand at room temperature for 2 hr. The mixture was made basic with aqueous sodium carbonate solution and the products were isolated with hexane. (This hydration procedure was necessary as extensive dehydro Mannich base was generated in all the manipulations; particularly in the oxalate recrystallization).

The crude extract (≈19 g.) in acetone (50 ml.) was added to oxalic acid (6 g.) in more acetone (50 ml.).

Recrystallization of the precipitate (15.8 g., m.p. 75°–78°) from methyl ethyl ketone gave a further quantity of pure oxalate salt (12.9 g.) $[\alpha]_D$ –23.6° (c =3.19, methanol).

[Note: Both the melting points and the rotations of the oxalate salts are dependent on the severity of the drying. This is probably due to the possible formation of solvates.]

EXAMPLE 20

2S,6R-2-[2-(R-α-phenethylamino)ethyl]-6-(4,4-phenylenedioxypentyl)tetrahydropyran-2-ol The procedure of Example 19 was repeated with the enantiomeric amine (R)-α-phenethylamine. Thus, the lactone (±)-9,9-phenylenedioxy-5-hydroxy-decanoic acid lactone (54 g, 80–90 percent purity) generated a crude base (~90 g.) which was processed as follows.

The crude product was partitioned between methanol-water-hexane-acetic acid (300:300:50:350 ml.). The hexane extract was washed with methanol-water-acetic acid (100 ml; 1:1:0.2). The combined "aqueous" phases were then extracted with hexane/benzene mixture (400 ml; 2:1) and then made basic with cold aqueous caustic potash (4N; ~250 ml.) (gave bad emulsion). Extraction with hexane then gave the purified amine base (58 g.) as an amber colored oil. Crystallization from hexane gave pure 2S,6R-2-[2-(R-α-phenethylamino)ethyl]-6-(4,4-phenylenedioxypentyl)-tetrahydropyran-2-ol (17.7 g; after combining other crops), m.p. 75°–77°, $[\alpha]_D$ +37° (c = 1.053; benzene).

Anal. Calcd. for $C_{26}H_{35}NO_4$: C, 73.38; H, 8.29; N, 3.29. Found: C, 73.63; H, 8.41; N, 3.26.

All the hexane mother liquors were taken to dryness (37 g.), dissolved in acetone (100 ml.) and added to oxalic acid (14 g.) dissolved in acetone (100 ml.). The solid formed (31 g.) was recrystallized from methyl ethyl ketone (250 ml.) to give 2R,6S-2-[2-(R-α-phenethylamino)-ethyl]-6-(4,4-phenylenedioxypentyl)tetrahydropyran-2-ol oxalate (26.6 g.), m.p. 81°–83° $[\alpha]_D$+22.7° (c = ~4; methanol).

Anal. Calcd. for $C_{26}H_{35}NO_4(CO_2H)_2$: C, 65.23; H, 7.23; N, 2.72. Found: C, 65.31; H, 7.31; N, 2.7.

EXAMPLE 21

3S,6aS-3-(4,4-phenylenedioxypentyl)-6a,β-methyl-1,2,3,5,6,6a-hexahydrocyclopenta[f][1]benzopyran-7,(8H)-one a. From 2S,6R-2-[2-(R-α-phenethylamino)ethyl]-6-(4,4-phenylenedioxypentyl)tetrahydropyran-2-ol The crystalline free base 2S,6R-2-[2-(R-α-phenethylamino)ethyl]-6-(4,4-phenylenedioxypentyl)-tetrahydropyran-2-ol (15.02 g.) was dissolved in a mixture of methanol (300 ml.) benzaldehyde (5.42 g.) and sodium bicarbonate (1.07 g.) and heated at reflux, under nitrogen, for 11 hr. The solvents were removed in vacuo and the residue was partitioned between ether and dilute aqueous hydrochloric acid (2N). The ether layer was then washed with aqueous sodium bisulfite solution (3 × 100 ml; 20 percent), brine and dried over sodium sulfate. Removal of the solvents in vacuo yielded the methanol adduct 2S-(2-methoxyethyl)-6R-(4,4-phenylenedioxypentyl)tetrahydropyran-2-ol (12.6 g.) as an oil $[\alpha]_D$ +8.94 (c = 1.6328, benzene) having ir bands (film) at 3475 (OH): 1712 (open ketohydroxy form); 1490, 1240 and 740 cm⁻¹ (catechol ketal). This compound presumably comprises the open and closed form tautomers. The crude methanol adduct (12.6 g.) was dissolved in a mixture of toluene (300 ml.), acetic acid (150 ml.), water (5 ml.) containing 2-methylcyclopentan-1,3-dione (4.47 g.) and heated at reflux for 8 hr. A Dean and Stark water trap was then attached and the mixture was heated at reflux for a further 90 min. The mixture was cooled, treated with benzene (500 ml.) and washed with water, aqueous sodium carbonate solution and dried over $MgSO_4$. Removal of the solvents in vacuo gave an orange colored gum (15.3 g.). Crystallization from isopropyl (12 ml; 90 percent) pyridine (6 ml.), 2-methylcyclopentan-1,3-dione (330 mg.) and heated at reflux under nitrogen for 16 hr. A Dean and Stark water trap was then attached and the water was separated for 35 min. Work up as in (a) above and filtration of the crude product through alumina (5 0 ml; grade III neutral) gave the dienol ether mixture (575 mg.) as a pale yellow solid. Crystallization from isopropyl alcohol gave 3S,6aS-3-(4,4-phenylenedioxypentyl)-6a,β-methyl-1,2,3,5,6,6a-hexahydrocyclopenta[f][1]benzopyran-7,(8)-one as needles (397 mg.) $[\alpha]_D$ –119° (c = ~2; chloroform); recrystallization raised the rotation to $[\alpha]_D$ –121°.

EXAMPLE 22

C/D-trans-3-(4,4-phenylenedioxypentyl)-6a,β-methyl-1,2,3,5,6,6a,7,8,9,9a-decahydrocyclopenta[f][1]benzopyran-7β-ol The dienol ether 3S,6aS-3-(4,4-phenylenedioxypentyl)-6a,β-methyl-1,2,3,5,6,6a-hexahydrocyclopenta[f][1]benzopyran-7,(8H)-one (14 g.) dissolved in THF (100 ml.) was added to a slurry of lithium aluminum hydride (5 g.) in THF (100 ml.) at 5°C. After stirring for 2 hr. at room temperature wet ether (200 ml.) and saturated aqueous sodium sulfate solution (30 ml.) was added. After stirring a further 1 hr. at room temperature the solids were filtered off and washed with ether. After drying the combined filtrate over $MgSO_4$ the solvents were taken to dryness in vacuo to yield a glass (15.5 g.). This material was dissolved in dry THF (100 ml.), treated with 5 percent Pd/C (1.5 g.) and hydrogenated at room temperature and pressure. After one mole of hydrogen had been consumed (usually 2-8 hr. required), the solids alcohol (140 ml.) gave the dienol ether 3S,6aS-3-(4,4-phenylenedioxypentyl)-6a,β-methyl-1,2,3,5,6,6a-hexahydrocyclopenta[f][1]benzopyran-7,(8H)-one (7.9 g.). Recrystallization gave pale orange needles (7.3 g.), m.p. 112°–113°, $[\alpha]_D$ –122.3° (c = 1.15; chloroform).

Anal Calcd. for $C_{24}H_{28}O_4$: C, 75.76; H, 7.42. Found C, 75.99; H, 7.63.

b. From 2S,6R-2-[2-(S-α-phenethylamino)ethyl]-6-(4,4-phenylenedioxypentyl)-tetrahydropyran-2-ol oxalate The oxalate salt ($\alpha_D$ –23.3°; 15.45 g.) was dissolved in methanol (360 ml.) containing sodium bicarbonate (6 g; anhydrous) and benzaldehyde (4.5 ml.) and heated under nitrogen at reflux for 16 hr. The methanol adduct was then worked up as in (a) above to yield the methanol adduct as a pale yellow colored oil (9.9 g.); ir (film) 3450(OH), 1700 (sat >C=O open hemiketal), 1480, 1260, 770 (catechol ketal), 1100 cm⁻¹ (methoxy). Conversion of this product to the dienol ether followed the procedure of (a) above and gave pure 3S,6aS,3-(4,4-phenylenedioxypentyl)-6a,β-methyl-1,2,3,5,6,6a-hexahydrocyclopenta [f][1]benzopyran-7,(8H)-one (5.5 g.) $[\alpha]_D$ –121° (c = ~2; chloroform).

c. Direct conversion of 2S,6R-2-[2-(R-α-phenethylamino) ethyl]-6-(4,4-phenylenedioxypentyl)tetrahydropyran-2-ol A total of 850 mg. of 2S,6R-2-[2-(R-α-phenethylamino) ethyl]-6-(4,4-phenylenedioxypentyl)tetrahydropyran-2-ol was dissolved in a mixture of toluene (30 ml.), aqueous acetic acid were filtered off, washed with more THF and the combined filtrates taken to dryness in vacuo. This gave a mixture of the above-titled enol ethers (15 g.). The nmr spectrum showed two methyl signals for the $C_{6a}$ methyl indicating ~3:1 mixture of the C/D trans to the C/D cis isomers.

EXAMPLE 23

(+)-6-(3,3-phenylenedioxybutyl)-3a,β-methyl-4,5,8,9,9a,9b-hexahydro-1H-benz[e]indene-3,7-(2H,3aH)-dione The crude enol-ether mixture C/D trans-3-(4,4-phenylenedioxypentyl)-6a,β-methyl-1,2,3,5,6,6a,7,8,9,9a-decahydrocyclopenta[f][1]benzopyran-7β-ol (15 g.) dissolved in acetone (150 ml.) was treated with aqueous sulfuric acid (0.5N; 50 ml.) at room temperature for 2 hr. (followed by tlc). Brine (500 ml.) was added and the products were isolated with ether to give a glass which contained a major amount of 3-(4,4-phenylenedioxypentyl)-4-hydroxy-6aβ-methyl-perhydrocyclopenta[f][1]benzopyran-7β-ol. This material dissolved in acetone (300 ml.) was cooled to 0°–5° and treated over 20 min. with fresh Jones chromic acid mixture (45 ml.). The mixture was then stirred an additional 2½ hr. at room temperature. Aqueous sodium bisulfite solution (100 ml; 10 percent) and brine (250 ml.) were added and the products were isolated by extraction with benzene. The combined benzene extracts were washed with dilute sodium carbonate solution (5 percent; 100 ml.) and taken to dryness in vacuo. The crude triketone 4-(3-oxo-7,7-phenylenedioxyoctyl)-1aβ-methyl-perhydroindan-1,5-dione (13.3 g.) showed strong bands in the infra red spectrum (chloroform) at 1735 and 1710 and 1480 (catechol ketal) $cm^{-1}$ and no hydroxyl band. The crude triketone was dissolved in methanol (100 ml.) and added to a solution of potassium hydroxide (2 g.) in methanol (50 ml.) under nitrogen. The deep red colored solution was then heated at reflux for 90 min., treated with acetic acid (3 ml.) and taken to dryness. The residue was partitioned between benzene and sodium carbonate solution (5 percent) and gave the crude tricyclic material (+)-6-(3,3-phenylenedioxybutyl)-3a,β-methyl-4,5,8,9,9a,9b-hexahydro-1H-benz[e]indene-3,7-(2H,3aH)-dione on concentration to dryness (11.1 g.). Crystallization from methylene chloride: isopropyl ether mixture (10:30) gave crystalline material (6.43 g.). This material was dissolved in ethanol (50 ml.) and left at room temperature, twice filtered free of solids (~20 min. intervals) and then cooled to 5° and seeded with pure product. After 16 hr. (at 0°–5°) the solids were isolated (4.5 g.), m.p. 118°–120°, $[\alpha]_D$ +40.34° (c = ~2; chloroform). From the various mother liquors a further quantity of material (1.06 g.) was obtained, m.p. 116°–119° $[\alpha]_D$ +40.39° (c = ~2; chloroform).

A sample of the bulked material was filtered through alumina (neutral, grade III) in benzene and recrystallized from ethanol to yield the analytical sample of (+)-6-(3,3-phenylenedioxybutyl)-3a,β-methyl-4,5,8,9,9a,9b-hexahydro-1H-benz[e]indene-3,7-(2H,3aH)-dione, m.p. 117°–119°, $[\alpha]_D$ +40.77 (c = 1.7267, chloroform).

Anal. Calcd. for $C_{24}H_{28}O_4$: C, 75.76; H, 7.42. Found: C, 75.96; H, 7.31.

EXAMPLE 24

(+)-19-Nor-androst-4-ene-3,17-dione

The tricyclic compound (+)-6-(3,3-phenylenedioxybutyl)-3a,β-methyl-4,5,8,9,9a,9b-hexahydro-1H-benz[e]indene-3,7-(2H,3aH)-dione (3.8 g; $[\alpha]_D$ +40.34°) was dissolved in THF (35 ml.) containing triethylamine (0.7 ml.) and 5 percent Pd/C (0.4 g.) and hydrogenated at room temperature and pressure until one mole equivalent of hydrogen had been consumed. The solids were filtered off and the filtrate was taken to dryness in vacuo to yield a colorless glass. This material was dissolved in ethanol (30 ml.), treated with aqueous hydrochloric acid (2N; 20 ml.) and heated at reflux under nitrogen for 4 hr. The solvents were partially removed in vacuo and the residue was extracted with benzene. The combined benzene extracts were washed with aqueous sodium carbonate solution (10 percent) and sodium hydroxide solution (1N). Removal of the solvents gave a white solid (2.8 g.), $[\alpha]_D$ +125° (c = 2.2°, chloroform). Recrystallization from methylene chloride-isopropyl ether mixture gave crystalline material (2.08 g.), m.p. 169°–172° (hot stage); 168°–170° (Hoover) $[\alpha]_D$ +139.5° (c = 3.03; chloroform). Recrystallization from aqueous methanol gave pure (+)-19-nor-androst-4-ene-3,17-dione (1.86 g.), m.p. 172°–174° (hot stage) and 168°–170° (Hoover) $[\alpha]_D$ +141.9°.

EXAMPLE 25

4,4-(2,3-Naphthalenedioxy)-1-chloropentane

A mixture of 2,3-naphthalenediol (13.3 g.) and 5-chloro-2-pentanone (5 g.) in benzene (100 ml.) containing p-toluenesulfonic acid (100 mg.) was heated at reflux under nitrogen in conjunction with a Dean and Stark water trap for 18 hr. The cold reaction mixture was treated with benzene (100 ml.) and washed with aqueous sodium carbonate solution (3 × 30 ml; 10 percent), brine and dried over magnesium sulfate (MgSO₄. anhydrous). The solids were filtered off and the filtrate was passed through a column of alumina (25 ml; neutral grade III). Removal of the solvents in vacuo gave an oil (7.3 g.) which yielded pure 4,4-(2,3-naphthalenedioxy)-1-chloropentane (5.4 g.) on distillation, b.p. 139°–141°/0.07 mm.

Anal. calcd. for $C_{15}H_{15}O_2Cl$; C, 68.57; H, 5.75; Cl, 13.49. Found: C, 68.41; H, 5.67; Cl, 13.49.

EXAMPLE 26

4,4-(4,5-Dimethylphenylenedioxy)-1-chlorpentane

A mixture of 4,5-dimethylcatechol (34.4 g.) and 5-chloro-2-pentanone (30 g.) in benzene (600 ml.) containing p-toluenesulfonic acid (600 mg) was heated, under nitrogen, at reflux in conjunction with a Dean and Stark water trap for 18 hr. More benzene (300 ml.) was added and the dark colored mixture was washed with aqueous sodium carbonate solution (3 × 150 ml; 10 percent), brine (250 ml.) and dried over MgSO₄. Removal of the benzene in vacuo gave a dark colored oil which was dissolved in hexane and filtered through alumina (175 ml; neutral grade III).

Removal of the solvent and distillation of the pale yellow colored oil (47.4 g.) yielded pure 4,4-(4,5-dimethylphenylenedioxy)-1-chloropentane after distillation (39.8 g.), b.p. 110°–120°/0.1 mm.

Anal. Calcd. for $C_{13}H_{17}O_2Cl$: C, 64.86; H, 7.12; Cl, 14.73. Found: C, 64.66; H, 7.3; Cl, 14.74.

EXAMPLE 27

(±)-6-[4,4-(2,3-Naphthalenedioxy)pentyl]-tetrahydropyran-2-ol

Magnesium metal (3 g; powder) was activated with iodine under nitrogen and treated with a solution (70 ml.) of the 4,4-(2,3-naphthalenedioxy)-1-chloropentane in tetrahydrofuran (THF) (20 g. in 200 ml. THF; distilled from calcium hydride). The mixture was heated to 40° and treated with dibromoethane (~.3 ml.). After the initial exotherm (slight) had subsided the rest of the solution was added. The mixture was then heated at 35°–37° for a further 3½–4 hr. with stirring. (The progress of the reaction was followed by quenching an aliquote (0.5 ml.) with aqueous ammonium chloride solution (2 ml; 15 percent and ether (0.5 ml.) and analyzing the organic phase by vpc at 200°C.) Dry redistilled glutaraldehyde (7.6 g.) dissolved in THF (60 ml.) was cooled to −60° and treated with the above Grignard reagent (10–15 min.) keeping the temperature at −60° → −50°. The mixture was then warmed to room temperature over ~ 3 hr. After this time (tlc indicated complete reaction) the mixture was cooled to 5° and treated with aqueous ammonium chloride solution (45 ml; saturated). The solids were filtered off, washed well with more THF and the combined filtrate was taken to dryness in vacuo. The crude hemiacetal (±)-6-[4,4-(2,3-naphthalenedioxyl)pentyl]-tetrahydropyran-2-ol (24.7 g.) was chromatographed on silica gel (750 g; 0.2–0.5 mm mesh) and yielded pure product (15.6 g.) on elution with benzene-ethyl acetate mixtures (9:1; 4:1 and 7:3).

Anal. Calcd. for $C_{20}H_{24}O_4$: C, 73.14; H, 7.37. Found: C, 72.84; H, 7.67.

Ir showed bands at 3600 (—OH), 1470 and 1250 $cm^{-1}$ (naphthalenedioxy).

EXAMPLE 28

(±)-6-[4,4-(4,5-dimethylphenylenedioxy)pentyl]-tetrahydropyran-2-ol

The chloroketal 4,4-(4,5-dimethylphenylenedioxy)-1-chlorpentane (24 g.) in THF (400 ml.) was converted into the Grignard reagent with magnesium (3.65 g.) as in Example 27. The above solution was then added to dry redistilled glutaraldehyde (10 g.) in THF (150 ml.) as before to yield the crude hemiacetal (±)-6-[4,4-(4,5-dimethylphenylenedioxy)pentyl]-tetrahydropyran-2-ol (32.5 g.) after the same workup. Chromatography on silica gel (900 g; 0.2–0.5 mm mesh) yielded pure material (13.8 g.).

Anal. Calcd. for $C_{18}H_{26}O_4$: C, 70.56; H, 8.55 Found: C, 69.73; H, 8.27.

Ir showed bands at 3600 (—OH), 1500 and 1260 $cm^{-1}$ (Phenylenedioxy).

EXAMPLE 29

(±)-11,11-(2,3-naphthalenedioxy)-3,7-dihydroxy-1-dodecene

The hemiacetal (±)-6-[4,4-(2,3-naphthalenedioxy)-pentyl]-tetrahydropyran-2-ol (15 g.) dissolved in THF (60 ml.) was cooled to 5° and treated with a solution of vinyl magnesium chloride (62.4 ml; 2.2 molar in THF) and stirred at room temperature overnight (2–3 hr. are sufficient). Aqueous ammonium chloride solution (30 ml; 15 percent) was added and the solids were filtered off and washed with more THF. The combined THF filtrates were taken to dryness in vacuo to yield the crude vinyl diol (±)-11,11-(2,3-naphthalenedioxy)-3,7-dihydroxy-1-dodecene (17.2 g.). Chromatography on silica gel (510 g; 0.2–0.5 mm mesh) gave pure product (13.3 g.) on elution with benzene-ethyl acetate mixtures (7:3; 1:1 and 1:3).

Anal. Calcd. for $C_{22}H_{28}O_4$: C, 74.13; H, 7.92. Found: C, 73.75; H, 7.80.

EXAMPLE 30

(±)-11,11-(4,5-dimethylphenylenedioxy)-3,7-dihydroxy-1-dodecene

The hemiacetal (±)-6-[4,4-(4,5-dimethylphenylenedioxy)pentyl]-tetrahydropyran-2-ol (13.7 g.) dissolved in THF (70 ml.) was treated with vinyl magnesium chloride solution (60.5 ml; 2.0 molar in THF) as in Example 29. Workup and chromatography on silica gel as in the previous example gave the pure vinyl diol (±)-11,11-(4,5-dimethylphenylenedioxy)-3,7-dihydroxy-1-dodecene (11.2 g).

Anal. Calcd. for $C_{20}H_{30}O_4$: C, 71.83; H, 9.04. Found: C, 71.79; H, 9.27.

IR shows bands at 3610 and 3450 (-OH), 1500 and 1255 (phenylenedioxy) and 860 $cm^{-1}$ ($C=CH_2$).

EXAMPLE 31

(±)-2-(2-diethylaminoethyl)-4,4-(2,3-naphthalenedioxy)pentyltetrahydropyran-2-ol Manganese dioxide (140 g.) was added to benzene (400 ml.) and cooled to ~5°. Diethylamine (400 ml.) was slowly added followed by a solution of the vinyl diol (±)-11,11-(2,3-naphthalenedioxy)-3,7-dihydroxy-1-dodecene (14.4 g.) in benzene (100 ml.). The mixture was stirred at room temperature for 18 hr., filtered free of solids and the residue was washed well with benzene. Removal of the benzene from the combined extracts gave a brown colored oil (21.2 g.). This material was dissolved in ether (200 ml.) and extracted with cold aqueous hydrochloric acid (1N; 4 × 50 ml.). The aqueous phase was made basic with caustic potash solution (2N) and the product was isolated with ether. Removal of the solvents yielded (±)-2-(2-diethylaminoethyl)-4,4-(2,3-naphthalenedioxy)pentyl-tetrahydropyran-2-ol (16.2 g.) as an amber colored oil.

Ir had bands at 3600 (bonded -OH and -NH) 1250 and 1470 $cm^{-1}$ (naphthalenedioxy).

EXAMPLE 32

(±)-2-(2-diethylaminoethyl)-6-[4,4-dimethylphenylenedioxy)pentyl]-tetrahydropyran-2-ol A solution of the vinyl diol (±)-11,11-(4,5-dimethylphenylenedioxy)-3,7-dihydroxy-1-dodecene (11.5 g.) in benzene (100 ml.) was treated with manganese dioxide (115 g.) as in Example 31. After acid purification the product (±)-2-(2-diethylaminoethyl)-6-[4,4-dimethylphenylenedioxy)pentyl]-tetrahydropyran-2-ol (11.6 g.) was obtained as a pale yellow oil.

Anal. Calcd. for $C_{24}H_{39}NO_4$: C, 71.07; H, 9.69; N, 3.45. Found: C, 70.87; H, 9.74; N, 3.15.

IR showed bands at 3100 (broad, bonded -OH and —NH) 1500 and 1260 cm$^{-1}$ (phenylenedioxy).

EXAMPLE 33

(±)-3-[4,4-(2,5-Naphthalenedioxy)pentyl]-6aβ-methyl-1,2,3,5,6,6a-hexahydro-cyclopenta-[f][1]-benzopyran-7(8H)-one A mixture of (±)-2-(2-diethylaminoethyl)-4,4-(2,3-naphthalenedioxy)pentyl-tetrahydropyran-2-ol (1.51 g.), toluene (8 ml.), acetic acid (2 ml.) and 2-methylcyclopentan-1,3-dione (470 mg.) was heated at reflux, under nitrogen for 90 min. Dilution with benzene (50 ml.) and extraction with water, aqueous sodium carbonate solution and brine yielded the dienol ether (1.5 g.) as an orange-yellow colored oil. A sample of this material was filtered through a column of alumina (grade III; neutral; 10:1) in benzene-hexane (1:1) mixture. Removal of the solvents in vacuo and crystallization of the pale yellow colored residue from hexane furnished pure (±)-3-[4,4-(2,5-naphthalenedioxy)pentyl]-6aβ-methyl-1,2,3,5,6,6a-hexahydro-cyclopenta-[f][1]benzopyran-7(8H)-one, m.p. 112°–114°.

Anal. Calcd. for $C_{29}H_{30}O_4$: C, 78.11; H, 7.02. Found: C, 78.36; H, 7.30.

EXAMPLE 34

(±)-3-[4,4-(4,5-Dimethylphenylenedioxy)pentyl]-6aβ-methyl-1,2,3,5,6,6a-hexahydrocyclopenta[f][1]benzopyran-7(8H)-one A mixture of (±)-2-(2-diethylaminoethyl)-6-[4,4-dimethylphenylenedioxy)pentyl]-tetrahydropyran-2-ol (11.5 g.), toluene (60 ml.), acetic acid (15.2 ml.) and 2-methylcyclopentane-1,3-dione (3.6 g.) was heated at reflux for 1 hour and then 30 min. more in conjunction with a Dean and Stark water trap. Workup as in Example 33 gave the dienol ether as a brown-red colored solid (11.1 g.). A sample of this material after filtration through alumina (neutral; grade III) yielded pure (±)-3-[4,4-(4,5-dimethylphenylenedioxy)pentyl]-6aβ-methyl-1,2,3,5,6,6a-hexahydrocyclopenta[f][1]benzopyran-7(8H)-one on crystallization from hexane, m.p. 125°–127°.

Anal. Calcd. for $C_{26}H_{32}O_4$: C, 76.44; H, 7.90. Found: C, 76.23; H, 7.95.

EXAMPLE 35

C/D-trans-3-[4,4-(2,3-naphthalenedioxy)pentyl]-6aβ-methyl-1,2,3,5,6,6a,7,8,9,9a-decahydrocyclopenta[f][1]benzopyran-7β-ol The crude dienol ether (±)-3-[4,4-(2,5-naphthalenedioxy)pentyl]-6aβ-methyl-1,2,3,5,6,6a-hexahydro-cyclopenta[f][1]benzopyran-7(8H)-one (11.7 g.) dissolved in THF (120 ml.) was cooled to 5° and treated, dropwise with sodium-bis-(2-methoxyethoxy)aluminate (Fr. Pat. 1,515,582) (7.1 ml; 70 percent w/w in benzene). After stirring for a further 1 hr. at room temperature, ether (500 ml.) was added followed by dilute aqueous sodium hydroxide solution (2N; 100 ml.). The organic phase was washed with brine and dried over $MgSO_4$. Removal of the solvents in vacuo gave a glass comprising racemic 3-[4,4-(2,3-naphthalenedioxy)pentyl]-6aβ-methyl-1,2,3,5,6,6a,7,8-octahydrocyclopenta[f][1]benzopyran-7β-ol. This was one major spot on the tlc analysis and showed bands in the ir spectrum ($CHCl_3$ solution) at 3600 and 3450 (—OH), 1645 (dienol ether) and 1465 cm$^{-1}$ (naphthalenedioxy).

The crude material (11.6 g.) was dissolved in THF (200 ml.) containing 5 percent Pd/C (1 g.) and hydrogenated at room temperature and pressure until one mole of hydrogen had been consumed. The solids were filtered off washed well with more THF and the combined filtrates were taken to dryness in vacuo to give product (11.7 g.) as a glass which contained a major amount of C/D-trans-3-[4,4-(2,3-naphthalenedioxy)pentyl]-6aβ-methyl-1,2,3,5,6,6a,7,8,9,9a-decahydrocyclopenta[f][1]benzopyran-7β-ol.

This material was one major spot on tlc analysis and showed bands in the ir spectrum (film) at 3450 (—OH), 1675 (enol ether) 1470 and 1250 cm$^{-1}$ (naphthalenedioxy). The nmr spectrum showed two methyl signals at δ0.78 ppm in the ratio of approximately 85:15 indicating the relative amounts of C/D trans and C/D cis material respctively.

EXAMPLE 36

C/D-trans-3-[4,4-(4,5-dimethylphenylenedioxy)pentyl]-6aβ-methyl-1,2,3,5,6,6a,7,8,9,9a-decahydrocyclopenta[f][1]benzopyran-7β-ol Treatment of the dienol ether (±)-3-[4,4-(4,5-diemthylphenylenedioxy)pentyl]-6aβ-methyl-1,2,3,5,6,6a-hexahydrocyclopenta[f][1]benzopyran-7(8H)-one (9.8 g.) as in Example 35 yielded the crude alcohol racemic 3-[4,4-(4,5-dimethylphenylenedioxy)pentyl]-6aβ-methyl-1,2,3,5,6,6a,7,8-octahydrocyclopenta[f][1]benzopyran-7β-ol (10 g.) as a glass having bands in the ir spectrum at 3600 and 3450 (—OH) and 1645 cm$^{-1}$ (dienol ether). Hydrogenation as in Example 35 gave the enol ether C/D-trans-3-[4,4-(4,5-dimethylphenylenedioxy)pentyl]-6aβ-methyl-1,2,3,5,6,6a,7,8,9,9a-decahydrocyclopenta[f][1]benzopyran-7β-ol (10.4 g.) as a glass.

The nmr spectrum showed the methyl signals centered at δ0.74 ppm in an approximate ratio of 70:30 indicating the relative proportions of the C/D trans and C/D cis materials respectively.

EXAMPLE 37

(±)-6-[3,3-(2,3-Naphthalenedioxy)butyl]-3aβ-methyl-4,5,8,9,9a-9β-hexahydro-1H-benz[e]indene-3,7-(2H,3aH)-dione A solution of the crude enol ether C/D-trans-3-[4,4-(2,3-naphthalenedioxy)pentyl]-6aβ-methyl-1,2,3,5,6,6a,7,8,9,9a-decahydrocyclopenta[f][1]benzopyran-7β-ol (12.6 g.) in acetone (135 ml.) was treated with dilute aqueous sulfuric acid (13.4 ml; 1N) and left at room temperature for 2 hr. This solution of the crude hemiketal (±)-3-[4,4-(2,3-naphthalenedioxy)butyl]-4-hydroxy-6aβ-methyl-perhydrocyclopenta[f][1]benzopyran-7β-ol was then cooled to 5° and treated over 20 min. with a solution of sodium dichromate-sulfuric acid (34 ml; from 100 g. $Na_2Cr_2O_7.2H_2O$; 70.8 ml. $H_2SO_4$ conc. made up to 250 ml. with water).

The mixture was then warmed to room temperature and stirred at that temperature for a further 2 hr. Dilute aqueous sodium bisulfite solution was added (100 ml. 5 percent) followed by brine (100 ml.) and the organic materials were isolated with benzene. The combined benzene extracts were washed with an aqueous sodium carbonate solution (5 percent; 2 × 40 ml.) dried over $MgSO_4$ and taken to dryness in vacuo. This gave the triketone (±)-4-[3-oxo-7,7-(2,3-naphthalenedioxy)- octyl]-1aβ-methylperhydroindan-1,5-dione (9.6 g.) as an orange colored oil showing bands in the ir spectrum (CHCl₃ solution) at 1740 (cyclopentanone), 1710 (cyclohexanone and straight chain ketone) and 1470 cm$^{-1}$ (naphthalenedioxy).

The crude triketone (9.6 g.), dissolved in methanol, was added to a solution of potassium hydroxide (1.44 g.) dissolved in more methanol (36 ml.) and heated at reflux for 1½ hr. Glacial acetic acid (2.2 ml.) was added; the solvents were removed in vacuo and the residue was extracted into methylene chloride, washed with brine, aqueous sodium carbonate solution (5 percent) and dried with MgSO₄. Removal of the solvents in vacuo yielded the crude tricyclic material as a brown powder. Crystallization from chloroform-methanol mixture yielded pure (±)-6-[3,3-(2,3-naphthalenedioxybutyl]-3aβ-methyl-4,5,8,9,9a,9b-hexahydro-1H-benz[e]indene-3,7-(2H,3aH)-dione (3.9 g.), m.p. 247°–249°.

Anal. Calcd. for C₂₈H₃₀O₄: C, 78.12; H, 7.02. Found: C, 77.81; H, 6.87.

EXAMPLE 38

(±)-6-[3,3-(4,5-dimethylphenylenedioxy)butyl]-3aβ-methyl-4,5,8,9a,9b-hexahydro-1H-benz[e]-indene-3,7-(2H,3aHO)-dione The crude enol ether C/D-trans-3-[4,4-(4,5-dimethylphenylenedioxy)pentyl]-6aβ-methyl-1,2,3,5,6,6a,7,8,9,9a-decahydrocyclopenta[f][1]benzopyran-7β-ol (10.4 g.) in analogous fashion to Example 37 was hydrated to give the crude hemiketal (±)-3-[4,4-(4,5-dimethylphenylenedioxy)butyl]-4-hydroxy-6-aβ-methylperhydrocyclopenta[f][1]benzopyran-7β-ol. This compound was oxidized as before to yield the crude triketone (±)-4-[3-oxo-7,7-(4,5-dimethylphenylenedioxy)octyl]-1aβ-methyl-perhydroindan-1,5-dione showing bands in the ir spectrum (CHCl₃ solution) at 1735 (cyclopentanone), 1710 (cyclohexanone and straight chain ketone) and 1485 cm$^{-1}$ (phenylenedioxy). Cyclization of the triketone yielded the crude tricyclic material (±)-6-[3,3-(4,5-dimethylphenylenedioxy)butyl]-3aβ-methyl-4,5,8,9,9a,9b-hexahydro-1H-benz[e]-indene-3,7-(2H,3aH)-dione (4.7 g.) as an orange colored oil. Chromatography on 150 g. of silica gel using benzene-ethyl acetate mixtures (9:1 and 17:3) followed by cystallization from ethanol gave pure product (1.37 g.), m.p. 164°–165°.

Anal. Calcd. for C₂₆H₃₂O₄: C, 76.44; H, 7.90. Found: C, 76.20; H, 7.75.

EXAMPLE 39

(±)-6-[3,3-(2,3-Naphthalenedioxy)butyl]-3aβ-methyl-perhydrobenz[e]-indane-3,17-dione The tricyclic material (±)-6-[3,3-(2,3-naphthalenedioxy)butyl]-3aβ-methyl-4,5,8,9,9a,9b-hexahydro-1H-benz[e]indene-3,7-(2H,3aH)-dione (3.2 g.) was treated with 5 percent Pd/C (500 mg.) in THF (100 ml.) containing triethylamine (1 ml.) and hydrogenated at room temperature and pressure until one mole of hydrogen had been consumed. The solids were filtered off and the solvents removed in vacuo. Crystallization of a sample from ethanol yielded the saturated diketone, m.p. 190°–195°.

Anal. Calcd. for C₂₈H₃₂O₄: C, 77.75; H, 7.46. Found: C, 77.92; H, 7.32.

EXAMPLE 40

(±)-19-Nor-androst-4-ene-3,17-dione

A. A solution of (±)-6-[3,3-(2,3-naphthalenedioxy)-butyl]-3aβ-methyl-perhydrobenz[e]-indane-3,17-dione (2 g.) in n-butanol (60 ml.) was treated with dilute aqueous hydrochloric acid (20 ml; 4N) and heated at reflux for 4 hr. The solvents were removed in vacuo and the residue was extracted with ether. After washing the ethereal solution with aqueous sodium carbonate solution (10 percent) and caustic soda solution (1N) the solvents were removed in vacuo. Crystallization of the residue from methylene chloride-isopropyl ether mixture yielded racemic 19-nor-androst-4-ene-3,17-dione (1.06 g.), m.p. 155°–156° identical with authentic material (tlc; ir, uv).

Uv λ$_{max}$ 239 mμ ($ε_{max}$ 17,100); ir bands at 1738 (cyclopentanone) 1665 and 1620 cm$^{-1}$ (cyclohexenone).

B. A solution of (±)-6-[3,3-(4,5-dimethylphenylenedioxy)butyl]-3aβ-methyl-4,5,8,9a,9b-hexahydro-1H-benz[e]-indene-3,7-(2H,3aH)-dione (1.22 g.) in THF (50 ml.) containing triethylamine (0.5 ml.) and 5 percent Pd/C (300 mg.) was hydrogenated at room temperature and pressure until one mole of hydrogen was consumed. The solids were filtered off and the filtrate was taken to dryness in vacuo. The residue (1.3 g.), consisting of (±)-6-[3,3-(4,5-phenylenedioxy)butyl]-3aβ-methyl-perhydrobenz[e]indane-3,17-dione which showed bands in the ir (CHCl₃ solution) at 1735 (cyclopentanone), 1705 (cyclohexanone) and 1485 cm$^{-1}$ (phenylenedioxy), dissolved in ethanol (30 ml.) was treated with dilute aqueous hydrochloric acid (4N; 10 ml.) and heated under reflux for 4 hr. Removal of the solvents in vacuo and workup as before yielded (±)-19-nor-androst-4-ene-3,17-dione (615 mg.) on crystallization from methylene chloride-isopropyl ether mixture.

This material was again identical with authentic material (m.p., mixed m.p., tlc, ir, and uv spectra).

Uv λ$_{max}$ 239 mμ ($ε_{max}$ 17,000); ir showed bands at 1738 (cyclopentanone), 1665 and 1620 cm$^{-1}$ (cyclohexenone).

EXAMPLE 41

A mixture of pure "Mannich Base" from Example 14 (4.68 g.) acetone (50 ml.), methyliodide (10 ml.) and anhydrous potassium carbonate (6.0 g.) was stirred at r.t. for 18 hr. The precipitate was filtered off, washed well with acetone and the filtrate evaporated to dryness. The resulting residue was mixed with tertiary butyl alcohol (120 ml.), water (30 ml.) and 2-ethylcyclopentane-1,3-dione and refluxed for 24 hr. After cooling, the mixture was evaporated to dryness, diluted with benzene and extracted with saturated oxalic acid solution, saturated sodium bicarbonate solution and water. The aqueous layers were reextracted with benzene and the combined benzene layers were dried over anhydrous sodium sulfate. Filtration and solvent removal afforded a brown oil (4.5 g.). This material was chromatographed on silica gel (300 g.). Elution with benzene-ether 4:1, 2:1, 1:1, 1:2 and 1:4 afforded 3.77 g. of a colorless oil. This material was treated with p-toluenesulfonic acid (370 mg.; monohydrate) at room temperature. After stirring for 30 minutes the mixture was treated with more p-toluenesulfonic acid (370 mg.) and stirred at room temperature for 2 hr.

The solution was then extracted with brine, saturated sodium bicarbonate solution and brine again. The aqueous layers were extracted with benzene and the combined benzene layers dried over anhydrous sodium sulfate. Filtration and solvent removal afforded 3.32 g. of an oil, which was chromatographed on silica gel (300 g.). Elution with benzene: ether 9:1 and 4:1 afforded 3S,6aS, 3-(4,4-phenylenedioxypentyl)-6aβ-ethyl-1,2,3,5,6,6a-hexahydrocyclopenta[f][1]benzopyran-7(8H)-one, (2.69 g; 60% from Mannich Base) as an oil; $[\alpha]_D^{25} = -117.8°$ (C= 1.30 in $CHCl_3$).

EXAMPLE 42

A solution of the product from Example 41 (2.66 g.) in THF (30 ml.; dried over $Al_2O_3$, grade I) was added at 0°–5°C. (within 10 min.) to a mixture of lithium aluminumhydride (520 mg.) in THF (50 ml.), with stirring. The resulting mixture was stirred at room temperature for 1½ hr. and then worked up by careful addition of saturated aqueous sodium sulfate solution. Filtration and solvent removal afforded 3S,6aS,3-(4,4-phenylenedioxypentyl)-6aβ-ethyl-1,2,3,5,6,6a,7,8-octahydrocyclopenta[f][1]benzopyran-7β-ol (2.74 g.) as an oil.

EXAMPLE 43

A solution of the product from Example 42 (2.54 g.) in toluene (90 ml.) was hydrogenated under normal conditions using a palladium catalyst (300 mg.; "AK 4"). The uptake (145 ml.) of $H_2$ stopped after about 3 hr. The catalyst was filtered off and washed with benzene. Solvent removal gave trans-3S,6aS,3-(4,4-phenylenedioxypentyl)-6aβ-ethyl-1,2,3,5,6,6a,7,8,9-,9a-decahydrocyclopenta[f][1]benzopyran-7β-ol as an oil.

EXAMPLE 44

A mixture of the product from Example 43 (2.8 g.) acetone (26 ml.) and 0.5N sulfuric acid (2.6 ml.) was allowed to stand at room temperature for 2¾ hr. The reaction mixture containing trans-3S,6aS,3-(4,4-phenylenedioxypentyl)-6aβ-ethyl-perhydrocyclopenta[f][1]benzopyran-4,7β-diol was then cooled to 0°C. and treated with freshly prepared Jones Reagent (6.7 ml.). After addition, the mixture was stirred at room temperature for 4 hr., then diluted with benzene and the resulting mixture extracted with water, saturated sodium bicarbonate solution and brine. The aqueous layers were reextracted with benzene and the combined benzene layers dried over anhydrous sodium sulfate. Filtration and solvent removal afforded trans-1aS,4-(3-oxo-7,7-phenylenedioxyoctyl)-1aβ-ethyl-perhydroindan-1,5-dione (2.0 g.) as a brown oil.

EXAMPLE 45

A solution of the product from Example 44 (2.0 g.) in methanol (6.5 ml.) was treated with a solution of potassium hydroxide (210 mg.) in methanol (13.5 ml.) and then refluxed with stirring for 1½ hr. After cooling, the mixture was diluted with benzene and extracted with water, 0.5 N hydrochloric acid, saturated sodium bicarbonate solution and brine. The aqueous layers were reextracted wth benzene and the combined benzene layers dried over anhydrous sodium sulfate. Filtration and solvent removal afforded trans-anti-3aS,6-(3,3-phenylenedioxybutyl)-3aβ-ethyl-4,5,8,9,9a,9b-hexahydro-1H-benz[e]inden-3,7(2H,8H)-dione (1.46 g.) as an oil.

EXAMPLE 46

A solution of the product from Example 45 (1.46 g.) in ethanol (42 ml.) and triethylamine (2.0 ml.) was hydrogenated under normal conditions using a palladium catalyst (300 mg.; AK 4). The uptake (88 ml.) of $H_2$ stopped after 5 hr. The catalyst was filtered off and washed with ethanol. Solvent removal afforded trans-anti-trans-3aS,6-(3,3-phenylenedioxybutyl)-3aβ-ethyl-4,5,5a,6,8,9,9a,9b-octahydro-1H-benz[e]-inden-3,7-(2H,8H)-dione (1.39 g.) as an oil.

EXAMPLE 47

A solution of the product from Example 46 (1.39 g.) in ethanol (39 ml.) and 2N hydrochloric acid (19 ml.) was refluxed for 4 hr. After cooling, the mixture was concentrated in vacuo, then diluted with benzene and extracted with water, 10% aqueous sodium carbonate solution, 10% aqueous sodium hydroxide solution and brine. The aqueous layer was reextracted with benzene and the combined benzene layers dried over anhydrous sodium sulfate. Filtration and solvent removal afforded 1.0 g. of an oil. This material was chromatographed on alumina (grade III, 100 g.). The column was prepared in a hexane-benzene mixture 4:1. Elution with hexane-benzene 1:9, benzene alone and benzene-ether 9:1 afforded 550 mg. of a semi-crystalline product. This material was crystallized from isopropyl ether-hexane at 0°C. to afford d-(+)-13β-ethylgon-4-en-3,17-dione, 337.4 mg., as colorless crystals. An optically pure sample was obtained by fractional recrystallization of the above sample from ethanol and methanol. The analytically pure sample had a m.p. of 176.5°–178°C. and $[\alpha]_D^{25} = +98.13°$ (C= 1.0374, $CHCl_3$).

Calcd. for $C_{19}H_{26}O_2$: C, 79.68; H, 9.15 (286.40) Found: C, 79.89; H, 9.26.

Uv max (e) at 239 mμ, ∊16250; ir $CHCl_3$ showed absorptions at 1740 $cm^{-1}$ (cyclopentanone), 1660 and 1620 $cm^{-1}$ (unsaturated ketone). Nmr (A 60, $CDCl_3$) triplet, 3 protons $C_{18}$—$CH_3$, centered at δ0.80, J= 8 cps; singlet, 1 proton $C_4$—H, at δ5.85.

We claim:

1. The compounds of the formula

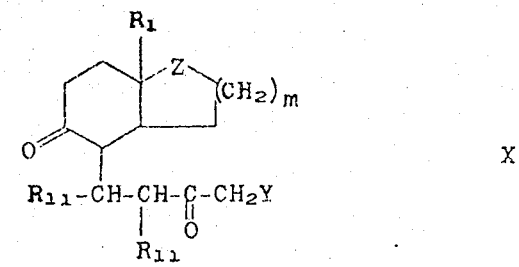

X wherein Y is

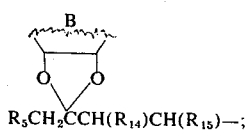

$R_5CH_2\overset{B}{C}CH(R_{14})CH(R_{15})—$;

B is the remaining residue of a hydrocarbyl group which may be monocyclic or bicyclic and which may bear one or more additional substituents selected from the group consisting of lower alkyl or lower alkoxy; $R_1$ is a primary alkyl group of from 1 to 5 carbon atoms; $R_5$, $R_{11}$, $R_{12}$, $R_{14}$ and $R_{15}$ are each independently hydrogen or lower alkyl; Z is carbonyl or a group of the formula

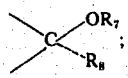

$R_7$ is hydrogen or lower carboxylic acyl; $R_8$ is hydrogen or lower aliphatic hydrocarbyl and $m$ is an integer having a value of 1 to 2 and optical enantiomers thereof.

2. The compounds of claim 1 wherein Y is selected from the group consisting of 3,3-(phenylenedioxy)-butyl; 3,3-(2,3-naphthalenedioxy)-butyl and 3,3-(4,5-dimethyl-phenylenedioxy)-butyl.

3. The compound of claim 2 which is 4-(3-oxo-7,7-phenylenedioxyoctyl)-1a,β-methyl-perhydroindan-1,5-dione and its optical enantiomers.

4. The compound of claim 2 which is 4-(3-oxo-7,7-phenylenedioxyoctyl)-1a,β-ethyl-perhydroindan-1,5-dione and its optical enantiomers.

* * * * *